(12) United States Patent
Doyle et al.

(10) Patent No.: US 8,673,320 B2
(45) Date of Patent: Mar. 18, 2014

(54) **METAL-CITRATE TRANSPORTER ANTIGEN FROM *STREPTOMYCES COELICOLOR* AND USES THEREOF**

(75) Inventors: Robert P. Doyle, Syracuse, NY (US); Joshua J. Lensbouer, Sommerset, PA (US)

(73) Assignee: Syracuse University, Syracuse, NY (US)

( * ) Notice: Subject to any disclaimer, the term of this patent is extended or adjusted under 35 U.S.C. 154(b) by 164 days.

(21) Appl. No.: 12/996,201

(22) PCT Filed: Jun. 8, 2009

(86) PCT No.: PCT/US2009/046590
§ 371 (c)(1),
(2), (4) Date: Mar. 9, 2011

(87) PCT Pub. No.: WO2009/149443
PCT Pub. Date: Dec. 10, 2009

(65) Prior Publication Data
US 2011/0189196 A1    Aug. 4, 2011

Related U.S. Application Data

(60) Provisional application No. 61/059,428, filed on Jun. 6, 2008.

(51) Int. Cl.
*A61K 39/02* (2006.01)
(52) U.S. Cl.
USPC ............................................. 424/234.1
(58) Field of Classification Search
None
See application file for complete search history.

(56) References Cited

U.S. PATENT DOCUMENTS

2003/0119018 A1*  6/2003  Omura et al. ............... 435/6

OTHER PUBLICATIONS

Cruse et al., Illustrated Dict. of Immunology, 2nd ed., CRC Press, 2003, p. 46, 166, 382.*
McGuinness et al. (Mol. Microbiol., 7:505-514, 1993).*
Moudallal et al. (EMBO Journal, 1:1005-1010, 1982).*
Abaza et al. (J. Prot. Chem., 11:433-444, 1992).*
Dow et al., Med. Hypothesis, 77:977-981, 2011.*
Bowie et al. (Science, 1990, 247:1306-1310).*
Greenspan et al. (Nature Biotechnology 7: 936-937, 1999).*
International Search Report and Written Opinion issued in PCT/US2009/046590, mailed Apr. 9, 2010.
Lensbouer et al., "Functional Characterization and Metal Ion Specificity of the Metal-Citrate Complex Transporter from *Streptomyces coelicolor*," *Journal of Bacteriology*, 190(16):5616-5623 (2008).
Bentley et al., "Complete genome sequence of the model actinomycete *Streptomyces coelicolor* A3(2)," *Nature*, 417(6885):141-147 (2002).
Krom et al., "Complementary Metal Ion Specificity of the Metal-Citrate Transporters CitM and CitH of *Bacillus subtilis*," *Journal of Bacteriology*, 182:6374-6381 (2000).
Blancato et al., "Functional characterization and Me2+ ion specificity of a Ca2+-citrate transporter from *Enterococcus faecalis*," *FEBS Letters*, 273:5121-5130 (2006).
Garmory et al, "ATP-Binding Cassette Transporters Are Targets for the Development of Antibacterial Vaccines and Therapies," *Infection and Immunity*, 72(12):6757-6763 (2004).
Velayudhan et al., "Iron acquisition and virulence in *Helicobacter pylori*: a major role for FeoB, a high-affinity ferrous iron transporter," *Molecular Biology*, 37(2):274-286 (2000).

* cited by examiner

*Primary Examiner* — Brian J Gangle
(74) *Attorney, Agent, or Firm* — David L. Nocilly; Bond Schoeneck & King, PLLC

(57) ABSTRACT

The present invention relates to an isolated antigen from *Streptomyces coelicolor* that is useful for developing, inter alia, vaccines against pathogenic bacteria of humans and animals. The present invention also relates to vaccines and antibodies developed using the isolated antigen. The present invention also relates to methods of using the antigen, vaccines, and antibodies of the present invention to detect, treat, and prevent infection and diseases associated with pathogenic bacteria.

5 Claims, 12 Drawing Sheets

FIG. 5

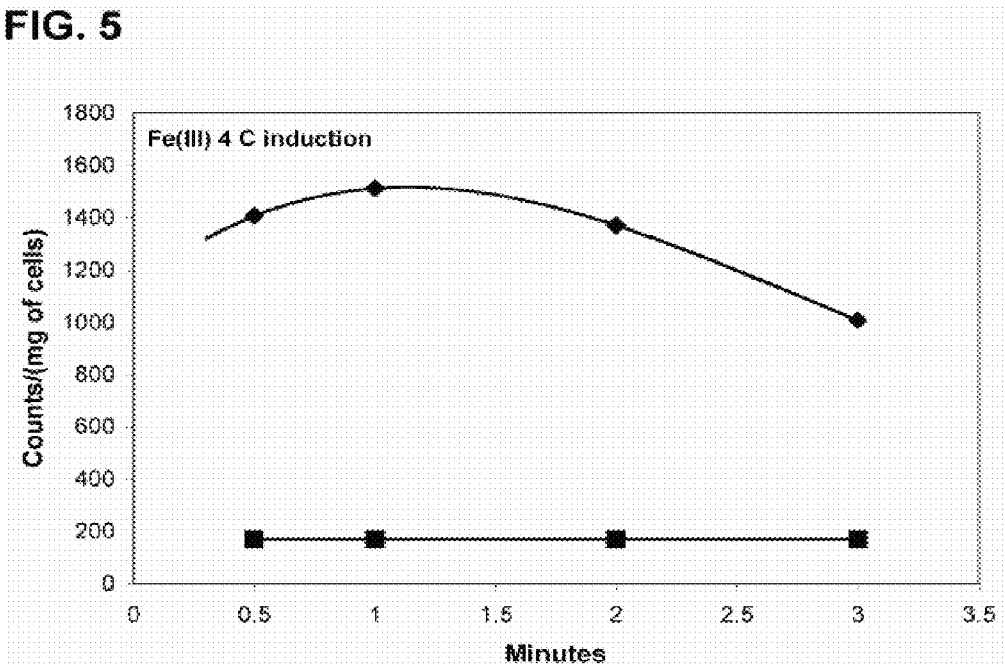

FIG. 6

| | | | |
|---|---|---|---|
| CitM | E. faecalis | IYLLLRLTG LDMGQWQKESAKYALGI FVIFVVTIVALGHMPLFIPQN | SEQ. ID NO. 13 |
| Cit$_{Sm}$ | S. mutans | IYLLLRLTGLDMGEWQKEAAKYALIIFV1FVVTIIAMGQMPLYIPQ- | SEQ. ID NO. 14 |
| CitM | B. subtilis | THLLVGLVGVSIDDHQKFALKWAVLAVIVMTAIALLIGAISISV--- | SEQ. ID NO. 15 |
| CitH | B. subtilis | TYLLVGMAGVSFGDHQKFTIKVVAVGTTIVMTIAALLIGIISF--- | SEQ. ID NO. 16 |
| Cit$_{Sc}$ | S coelicolor | 444- VYVLVGMAKVEFGDHTRFVVKVVAVLTSLVILAAGILFGII----483 | SEQ. ID NO. 17 |
| CitP | | LAASE<u>R</u>MNLIAFAQMGN---<u>R</u>IGGALILVVAGILVTFMK----- | SEQ. ID NO. 18 |
| CimH | | LSAAE<u>R</u>LELMPFAQVS----TRIGGAITVSLTLLLLHQFY---- | SEQ. ID NO. 19 |

SEQUENCE LISTING

<160> NUMBER OF SEQ ID NOS: 19

<210> SEQ ID NO 1
<211> LENGTH: 483
<212> TYPE: PRT
<213> ORGANISM: Streptomyces coelicolor

<400> SEQUENCE: 1

```
Met Leu Thr Ile Leu Gly Phe Ala Met Ile Ala Thr Phe Leu Val Leu
1               5                   10                  15

Ile Met Met Lys Lys Met Ser Pro Ile Ala Ala Leu Val Leu Ile Pro
            20                  25                  30

Ala Leu Phe Cys Val Leu Val Gly Lys Gly Ala His Leu Gly Asp Tyr
        35                  40                  45

Val Ile Asp Gly Val Ser Ser Leu Ala Pro Thr Ala Ala Met Leu Met
    50                  55                  60

Phe Ala Ile Val Tyr Phe Gly Val Met Ile Asp Val Gly Leu Phe Asp
65                  70                  75                  80

Pro Ile Val Arg Ala Ile Leu Lys Phe Cys Lys Ala Asp Pro Met Arg
                85                  90                  95

Ile Val Val Gly Thr Ala Leu Leu Ala Ala Ile Val Ser Leu Asp Gly
            100                 105                 110

Asp Gly Ser Thr Thr Phe Met Ile Thr Val Ser Ala Met Tyr Pro Leu
        115                 120                 125

Tyr Lys Arg Leu Lys Met Ser Leu Val Val Met Thr Gly Val Ala Ala
    130                 135                 140

Met Ala Asn Gly Val Met Asn Thr Leu Pro Trp Gly Gly Pro Thr Ala
145                 150                 155                 160

Arg Ala Ala Thr Ala Leu Lys Val Asp Ala Thr Asp Ile Phe Val Pro
                165                 170                 175

Met Ile Pro Ala Leu Ala Val Gly Leu Val Ala Val Val Leu Ala
            180                 185                 190

Tyr Val Leu Gly Leu Arg Glu Arg Arg Leu Gly Thr Leu Ser Leu
        195                 200                 205

Asp Gly Ala Pro Glu Arg Glu Pro Glu Thr Val Leu Val Gly
    210                 215                 220
```

```
Ala Gly Ala Gly Thr Gly Ala Ala Gly Leu Ser Gly Ala Gly Ala Gly
225                 230                 235                 240

Ala Gly Ala Gly Ala Ala Arg Gly Ala Ala Gly Gly Pro Gly Ala Ala
            245                 250                 255

Gly Asp Arg Asp Thr Gly Ala Gly Gly Glu Ser Asp Asp Phe Lys
        260                 265                 270

Gly Leu Asp Pro Asn Arg Pro Thr Leu Arg Pro Arg Leu Tyr Trp Phe
    275                 280                 285

Asn Ala Leu Leu Thr Leu Ala Leu Leu Thr Ala Met Ile Met Glu Leu
    290                 295                 300

Leu Pro Ile Pro Val Leu Phe Leu Ile Gly Ala Ala Leu Ala Leu Thr
305                 310                 315                 320

Val Asn Phe Pro His Ile Pro Asp Gln Lys Ala Arg Ile Ala Ala His
                325                 330                 335

Ala Asp Asn Val Leu Asn Val Ser Gly Met Val Phe Ala Ala Ala Val
            340                 345                 350

Phe Thr Gly Val Leu Thr Gly Thr Gly Met Val Asp His Met Ala Asn
        355                 360                 365

Trp Leu Val Asp Thr Ile Pro Asp Gly Met Gly Pro Gln Met Gly Leu
    370                 375                 380

Val Thr Gly Leu Leu Ser Leu Pro Leu Thr Tyr Phe Met Ser Asn Asp
385                 390                 395                 400

Gly Phe Tyr Phe Gly Val Leu Pro Val Leu Ala Glu Ala Gly Gln Ala
                405                 410                 415

His Gly Val Ser Thr Leu Glu Ile Ala Arg Ala Ser Ile Val Gly Gln
            420                 425                 430

Pro Leu His Met Ser Ser Pro Leu Val Pro Ala Val Tyr Val Leu Val
        435                 440                 445

Gly Met Ala Lys Val Glu Phe Gly Asp His Thr Arg Phe Val Val Lys
    450                 455                 460

Trp Ala Val Leu Thr Ser Leu Val Ile Leu Ala Ala Gly Ile Leu Phe
465                 470                 475                 480

Gly Ile Ile

<210> SEQ ID NO 2
<211> LENGTH: 1452
<212> TYPE: DNA
<213> ORGANISM: Streptomyces coelicolor

<400> SEQUENCE: 2
atgctgacca tcctcggctt cgccatgatc gcgaccttcc tggtcctgat catgatgaag    60
aagatgtcgc cgatcgcggc gctcgtgctg attcccgcgc tgttctgcgt gctcgtcggc   120
aagggcgccc atctcggcga ctacgtcatc gacggcgtgt ccagcctcgc ccccaccgcg   180
gcgatgctca tgttcgcgat cgtctacttc ggtgtgatga tcgacgtcgg gctcttcgac   240
ccgatcgtcc gggccatcct gaagttctgc aaggccgacc cgatgcgcat cgtcgtcggc   300
acggcgctgc tcgccgcgat cgtctcgctg gacggcgacg gctccaccac cttcatgatc   360
acggtctcgg cgatgtaccc gctgtacaag cggctgaaga tgagcctggt cgtgatgacc   420
ggcgtcgccg cgatggccaa cggcgtgatg aacacgctgc cctggggcgg ccccaccgcc   480
cgcgccgcca ccgcgctgaa ggtcgacgcc accgacatct tcgtcccgat gatcccggcc   540
ctggccgtgg gtctggtcgc ggtcgtcgtc ctggcgtacg tgctcggtct cgcgagcgc    600 aggcggctgg gcacgctgtc gctggacggg cgcccggagc gggagccgga gaccgagacg   660
```

-continued

```
gtgctggtcg gtgcgggcgc gggtacgggg gcggccgggc tttccggtgc gggtgcgggt      720
gcgggtgcgg gtgcggctcg cggcgcggcg ggcggcccccg gtgcggcggg cgaccgggac     780
accggggccg gcggcgagtc cgacgacgac ttcaagggcc tcgacccgaa ccggcccacc      840
ctgcggccca ggctgtactg gttcaacgcg ctgctcaccc tcgcgctgct caccgccatg      900
atcatggagc tgctgccgat cccggtgctc ttcctgatcg gcgccgcgct cgccctcacc      960
gtcaacttcc cgcacatccc ggaccagaag gcccgcatcg cggcccacgc cgacaacgtc     1020
ctcaacgtct ccggcatggt cttcgccgcc gccgtcttca ccggcgtcct caccggcacc     1080
ggcatggtcg accacatggc caactggctg gtggacacca tccccgacgg catgggcccg     1140
cagatgggcc tggtcaccgg cctgctgagc ctgccgctga cgtacttcat gtcgaacgac     1200
ggcttctact tcggcgtcct gccggtgctc gccgaggccg ccaggcgca cggcgtgtcg       1260 acgctggaga tcgcccgcgc ctcgatcgtc ggccagccgc tgcacatgtc cagcccgctc     1320
gtcccggccg tgtacgtcct ggtcggcatg gccaaggtcg agttcggcga ccacacgcgg     1380
ttcgtggtga agtgggccgt cctgacgagt ctggtgatcc tcgcggcggg catcctgttc     1440
ggcatcatct ga                                                         1452

<210> SEQ ID NO 3
<211> LENGTH: 31
<212> TYPE: DNA
<213> ORGANISM: Streptomyces coelicolor

<400> SEQUENCE: 3
cagccatggc actgaccatc ctcggccttc g                                    31

<210> SEQ ID NO 4
<211> LENGTH: 25
<212> TYPE: DNA
<213> ORGANISM: Streptomyces coelicolor

<400> SEQUENCE: 4
gatggatcct cagatgatgc cgaac                                           25

<210> SEQ ID NO 5
<211> LENGTH: 29
<212> TYPE: DNA
<213> ORGANISM: Streptomyces coelicolor

<400> SEQUENCE: 5
ggtgggatgt tcaagggcga acgttaggt                                       29

<210> SEQ ID NO 6
<211> LENGTH: 29
<212> TYPE: DNA
<213> ORGANISM: Streptomyces coelicolor

<400> SEQUENCE: 6 gggggggtggt gggttgtgat gtgttatgt                                      29

<210> SEQ ID NO 7
<211> LENGTH: 29
<212> TYPE: DNA
<213> ORGANISM: Streptomyces coelicolor

<400> SEQUENCE: 7
ggcgggaggt cggcatggac cggtagtgt                                       29
```

```
<210> SEQ ID NO 8
<211> LENGTH: 29
<212> TYPE: DNA
<213> ORGANISM: Streptomyces coelicolor

<400> SEQUENCE: 8
ggcgggccgg tacacccagg ctctaatct                                          29

<210> SEQ ID NO 9
<211> LENGTH: 19
<212> TYPE: DNA
<213> ORGANISM: Streptomyces coelicolor

<400> SEQUENCE: 9
gctgcttcgc gccacctaa                                                     19

<210> SEQ ID NO 10
<211> LENGTH: 19
<212> TYPE: DNA
<213> ORGANISM: Streptomyces coelicolor

<400> SEQUENCE: 10
ttaggttagg ctcacctaa                                                     19

<210> SEQ ID NO 11
<211> LENGTH: 19
<212> TYPE: DNA
<213> ORGANISM: Streptomyces pilosus

<400> SEQUENCE: 11
ttaggttagg ctcacctaa                                                     19

<210> SEQ ID NO 12
<211> LENGTH: 19
<212> TYPE: DNA
<213> ORGANISM: Corynebacterium diphtheriae

<400> SEQUENCE: 12
ttaggatagc tttacctaa                                                     19

<210> SEQ ID NO 13
<211> LENGTH: 47
<212> TYPE: PRT
<213> ORGANISM: Enterococcus faecalis

<400> SEQUENCE: 13

Ile Tyr Leu Leu Leu Arg Leu Thr Gly Leu Asp Met Gly Gln Trp Gln
1               5                   10                  15

Lys Glu Ser Ala Lys Tyr Ala Leu Gly Ile Phe Val Ile Phe Val Val
            20                  25                  30

Thr Ile Val Ala Leu Gly His Met Pro Leu Phe Ile Pro Gln Asn
        35                  40                  45

<210> SEQ ID NO 14
<211> LENGTH: 45
<212> TYPE: PRT
<213> ORGANISM: Streptococcus mutans

<400> SEQUENCE: 14

Ile Tyr Leu Leu Leu Arg Leu Thr Gly Leu Asp Met Gly Glu Trp Gln
1               5                   10                  15

Lys Glu Ala Ala Lys Tyr Ala Leu Ile Ile Phe Val Phe Val Val Thr
            20                  25                  30
```

-continued

Ile Ile Ala Met Gly Gln Met Pro Leu Tyr Ile Pro Gln
            35                  40                  45

<210> SEQ ID NO 15
<211> LENGTH: 44
<212> TYPE: PRT
<213> ORGANISM: Bacillus subtilis

<400> SEQUENCE: 15

Thr His Leu Leu Val Gly Leu Val Gly Val Ser Ile Asp Asp His Gln
  1               5                  10                  15

Lys Phe Ala Leu Lys Trp Ala Val Leu Ala Val Ile Val Met Thr Ala
                 20                  25                  30

Ile Ala Leu Leu Ile Gly Ala Ile Ser Ile Ser Val
             35                  40

<210> SEQ ID NO 16
<211> LENGTH: 43
<212> TYPE: PRT
<213> ORGANISM: Bacillus subtilis

<400> SEQUENCE: 16

Thr Tyr Leu Leu Val Gly Met Ala Gly Val Ser Phe Gly Asp His Gln
  1               5                  10                  15

Lys Phe Thr Ile Lys Val Val Ala Val Gly Thr Thr Ile Val Met Thr
                 20                  25                  30

Ile Ala Ala Leu Leu Ile Gly Ile Ile Ser Phe
             35                  40

<210> SEQ ID NO 17
<211> LENGTH: 41
<212> TYPE: PRT
<213> ORGANISM: Streptomyces coelicolor

<400> SEQUENCE: 17

Val Tyr Val Leu Val Gly Met Ala Lys Val Glu Phe Gly Asp His Thr
  1               5                  10                  15

Arg Phe Val Val Lys Val Val Ala Val Leu Thr Ser Leu Val Ile Leu
                 20                  25                  30

Ala Ala Gly Ile Leu Phe Gly Ile Ile
             35                  40

<210> SEQ ID NO 18
<211> LENGTH: 33
<212> TYPE: PRT
<213> ORGANISM: Leuconostoc mesenteroides

<400> SEQUENCE: 18

Leu Ala Ala Ser Glu Met Asn Leu Ile Ala Phe Ala Met Gly Asn Ile
  1               5                  10                  15

Gly Gly Ala Leu Ile Leu Val Val Ala Gly Ile Leu Val Thr Phe Met
                 20                  25                  30

Lys

<210> SEQ ID NO 19
<211> LENGTH: 33
<212> TYPE: PRT
<213> ORGANISM: Bacillus subtilis

<400> SEQUENCE: 19

Leu Ser Ala Ala Glu Leu Glu Leu Met Pro Phe Ala Val Ser Thr Ile
  1               5                  10                  15

```
Gly Gly Ala Ile Thr Val Ser Leu Thr Leu Leu Leu His Gln Phe
            20                  25                  30
Tyr
```

METAL-CITRATE TRANSPORTER ANTIGEN FROM *STREPTOMYCES COELICOLOR* AND USES THEREOF

CROSS-REFERENCE TO RELATED APPLICATIONS

This application is a U.S. National Phase filing under 35 U.S.C. 371 of International Application No. PCT/US2009/046590, filed Jun. 8, 2009, and published as WO 2009/149443 on Dec. 10, 2009, which claims priority to U.S. Provisional Patent Application Ser. No. 61/059,428, filed Jun. 6, 2008, the entire disclosures of which are hereby incorporated by reference in their entirety.

FIELD OF THE INVENTION

The present invention relates to an isolated antigen from *Streptomyces coelicolor* that is useful for developing, inter alia, vaccines against pathogenic bacteria of humans and animals. The present invention also relates to vaccines and antibodies developed using the isolated antigen. The present invention also relates to methods of using the antigen, vaccines, and antibodies of the present invention to detect, treat, and prevent infection and diseases associated with pathogenic bacteria.

BACKGROUND OF THE INVENTION

As used herein, certain citations to references are indicated as numerals or alphanumerical symbols in parentheticals or as superscripts, and are further described in the "References Cited" listing contained herein.

Citrate is a primary metabolite that is ubiquitously used as a source of carbon and energy by most living organisms. While there has been extensive research conducted into citrate transport across membranes (A21), there has been a relative dearth of research into membrane protein systems that can transport complexed citrate (A2). Currently, there is predicted to be over 90 members in the so-called CitMHS family of secondary transporters (A25). Members of this superfamily are found in Gram-positive bacteria and are predicted in Gram-negative bacteria. It is believed that these organisms take up complexed citrate, because it is predominantly available as such in their environment or to allow access to critical metal ions such as iron. To date, the only functionally characterized systems for metal-citrate transport in this family are those of *Bacillus subtilis* (A19), *Streptococcus mutans* (A20), and most recently *Enterococcus faecalis* (A4). These members of the CitMHS family transport metal-citrate complexes in symport with one $H^+$ per $M^{2+}$-citrate.

Lolkema et at demonstrated that CitM from *B. subtilis* transported citrate in complex with $Mg^{2+}$, $Ni^{2+}$, $Mn^{2+}$, $Co^{2+}$ and $Zn^{2+}$ but not in complex with $Ca^{2+}$, $Ba^{2+}$ and $Sr^{2+}$. CitH, also from *B. subtilis*, transported citrate and iso-citrate complexed to $Ca^{2+}$, $Ba^{2+}$ and $Sr^{2+}$ but not $Mg^{2+}$, $Ni^{2+}$, $Mn^{2+}$, $Co^{2+}$ and $Zn^{2+}$ (A19, A31). The group of metal ions transported by CitM includes the smaller cations, with a Pauling radius of less than ~0.80 Å. The ions transported by CitH of *B. subtilis* have radii larger than 0.98 Å. Neither transporter was shown to transport free citrate or metal complexes of other tri-carboxylates (or similar dicarboxylates) such as cis-aconitate and tricarballylate. More recently, Cvitkovitch et al. functionally characterized the CitM homolog from *Streptococcus mutans* (A20). Citrate complexed to $Fe^{3+}$ and $Mn^{2+}$ was transported with *S. mutans*, however $Ca^{2+}$, $Mg^{2+}$ and $Ni^{2+}$ were not. The CitH transporter of *Enterococcus faecalis* was characterized in 2006 (A4). High amino acid (AA) sequence homology to that of *S. mutans* led researchers to believe it could be using a CitMHS transporter to access iron. In fact this was shown not to be the case. The system was shown to be a CitM (*B. subtilis*) functional homolog, with larger ionic radii metals such as $Ca^{2+}$, $Sr^{2+}$, $Cd^{2+}$ and $Pb^{2+}$ involved in transport but not $Fe^{2+}$ or $Fe^{3+}$. This unpredictability clearly demonstrates the limited understanding of these systems.

Pathogenic bacteria are an important health concern worldwide. Some examples of pathogenic bacteria include *Bacillus anthracis*, *Mycobacterium tuberculosis*, *Corynebacterium diphtheriae*, *Neisseria meningitis*, and *Neisseria gonorrhoeae*. Pathogenic bacteria are also a health concern for animals. Because pathogenic bacteria cause infectious diseases, some of which cause millions of deaths worldwide each year, it is important that diagnostic tools and treatments that target pathogenic bacteria continue to be developed. A better understanding of the mechanisms by which pathogenic bacteria uptake nutrients and cause infection is needed to develop better prevention and treatement regimes against these bacteria.

The genome of *Streptomyces coelicolor* was sequenced in 2002 (A14). This effort identified an unprecedented number of genes encoding membrane-spanning transporters and gene sets that would encode enzymes for utilizing complex nutrients. The transporters on the *S. coelicolor* phylogenetic branch were found to share only between 35-45% amino acid (AA) sequence homology with those transporters investigated to date compared to 60-83% AA homology between the *B. subtilis*, *E. faecalis*, and *S. mutans* transporters. However, since 2002, there has been no reports on the identification and functional characterization of a metal-citrate transport of *S. coelicolor*. Thus, prior to the present invention, there was a need for such information, particularly since this information could lead to diagnostic tests and treatments for pathogenic bacteria.

The present invention is directed to the deficiencies in the art.

SUMMARY OF THE INVENTION

In one aspect, the present invention provides an isolated antigen that is useful for developing, inter alia, vaccines against pathogenic bacteria of humans and animals. The isolated antigen can include an isolated metal-citrate transporter from *Streptomyces coelicolor*. The isolated antigen can also include an isolated immunogenic polypeptide fragment of said metal-citrate transporter, where the immunogenic fragment retains an antigenic activity of said metal-citrate transporter.

In another aspect, the present invention provides a pharmaceutical composition that includes the isolated antigen and a pharmaceutically acceptable carrier.

In another aspect, the present invention provides a vaccine for immunizing an individual against a disease associated with a pathogenic bacteria. The vaccine includes an immunogenic amount of the isolated antigen of the present invention and a pharmaceutically acceptable carrier.

The present invention further provides an isolated antibody or antigen-binding fragment thereof that specifically binds with high affinity to the isolated antigen of the present invention.

In another aspect, the present invention provides a pharmaceutical composition that includes the antibody of the present invention and a pharmaceutically acceptable carrier.

The present invention further provides an isolated antisera containing the antibody of the present invention.

In another aspect, the present invention provides a diagnostic kit that includes the antibody of the present invention and a detecting agent for detecting binding by that antibody.

In yet a further aspect, the present invention provides a method for immunizing an individual against a disease associated with a pathogenic bacteria. In this method, an individual is administered a pharmaceutically effective amount of the vaccine of the present invention, thereby immunizing the individual against a disease associated with a pathogenic bacteria.

In another aspect, the present invention provides a method for inhibiting pathogenic bacteria infection of an individual. This method involves administering to an individual a pharmaceutically effective amount of the vaccine according to the present invention under conditions effective to inhibit iron uptake of the pathogenic bacteria from blood serum of the individual, thereby inhibiting infection of the individual by the pathogenic bacteria.

In one aspect, the present invention provides a method of treating or preventing pathogenic infection of an individual. This methods involves administering to an individual an effective amount of the antibody according to the present invention under conditions effective to inhibit iron uptake of the pathogenic bacteria from blood serum of the individual, thereby treating or preventing infection of the individual by the pathogenic bacteria.

The present invention further provides a method for detecting a pathogenic bacteria in a biological sample of an individual. This method involves collecting a biological sample from an individual and contacting the sample with the isolated antibody or antigen-binding fragment thereof of the present invention. A successful binding event between the isolated antibody or antigen-binding fragment thereof to at least one component of the sample is detected, where detection of the successful binding event indicates the presence of the pathogenic bacteria in the biological sample.

The present invention also provides a method for detecting the presence of a pathogenic bacteria on a surface. This method involves contacting the surface with the isolated antibody or antigen-binding fragment thereof of the present invention and detecting a successful binding event between the isolated antibody or antigen-binding fragment thereof to at least one component contained on the surface. Under this method, detection of the successful binding event indicates the presence of the pathogenic bacteria on the surface.

In another aspect, the present invention provides an isolated polynucleotide that encodes the antigen of the present invention.

In a further aspect, the present invention provides a vector that includes the isolated polynucleotide of the present invention.

The present invention also provides a host cell transformed with the vector of the present invention.

The present invention further provides a method for producing a metal-citrate transporter antigen from *Streptomyces coelicolor*. This method involves culturing the host cell of the present invention under conditions effective to produce the antigen, and then recovering the antigen from the culture.

Thus, in accordance with the present invention, a novel metal-citrate transporter antigen from *Streptomyces coelicolor* and fragments thereof are provided, and these antigens can thus be utilized in methods of generating antibodies capable of binding these antigens which can be useful in methods of treating or preventing uptake of iron in pathogenic bacteria. The present invention thus is directed to these proteins, antibodies capable of binding these proteins, methods of generating said antibodies, nucleic acids coding for said proteins, and pharmaceutical compositions or vaccines which include the proteins or antibodies of the present invention in combination with a pharmaceutically acceptable vehicle, carrier or excipient.

BRIEF DESCRIPTION OF DRAWINGS

FIG. 5 is a graph showing the uptake and metabolization of $Fe^{3+}$-citrate with Sccit induced with IPTG at 4° C. in *E. coli*.

FIG. 6 shows a multiple sequence alignment (using CLUSTALW[8]) residues from the C-terminal regions of CitM and CitH from *B. subtilis*, $Cit_{Sm}$, from *S. mutans* and $Cit_{Sc}$ from *S. coelicolor* A3(2). Two characterized 'free' citrate secondary transporters (CitP from *Leuconostoc mesenteroides*[7] and CimH from *B. subtilis*[9]) are shown, shaded, for comparison. Residues that will be explored by mutagenesis can be seen in FIG. 7. Residues are numbered relative to *S. coelicolor*.

DETAILED DESCRIPTION OF THE INVENTION

Figure 1A:
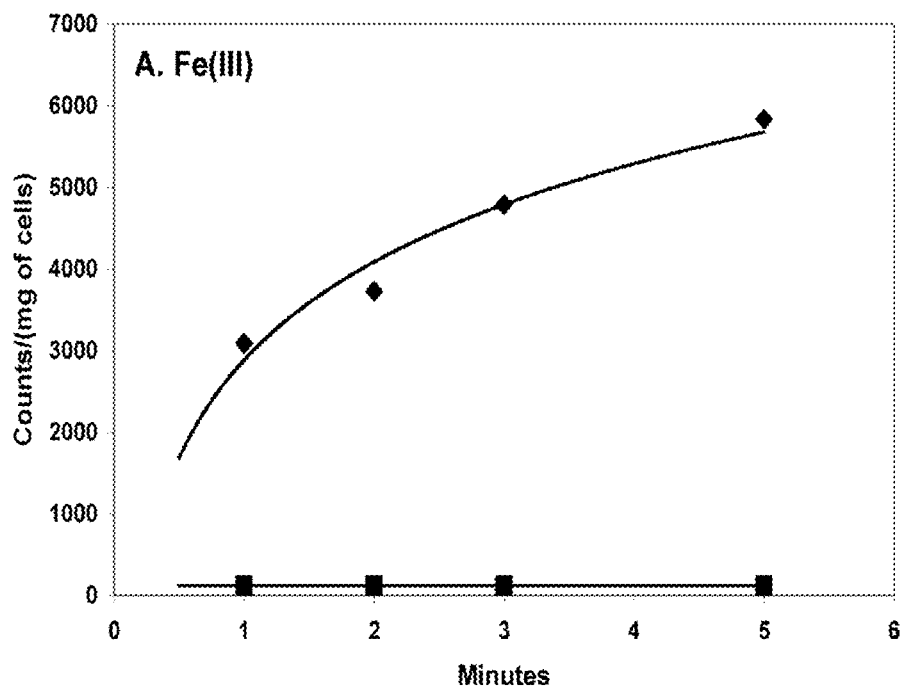
FIGS. 1A-1H are graphs showing the uptake of 1,5-[$^{14}$C]-citrate by *Streptomyces coelicolor* in the presence of different metal ions (υ). The uptake was measured in 50 mM Chelex washed PIPES buffer (pH 6.5) with 75 μM concentration of $Fe^{3+}$ (FIG. 1A), 10 mM concentration of $Ca^{2+}$ (FIG. 1B), $Pb^{2+}$ (FIG. 1C), $Ba^{2+}$ (FIG. 1E) and 1 mM concentrations of $Mn^{2+}$ (FIG. 1D), $Co^{2+}$ (FIG. 1F), $Mg^{2+}$ (FIG. 1G) and $Ni^{2+}$ (FIG. 1H). *S. coelicolor* was grown in SMMC broth. Metal free controls (i.e. 'free' citrate) are shown as contrast in each plot (υ).
Figure 1B:
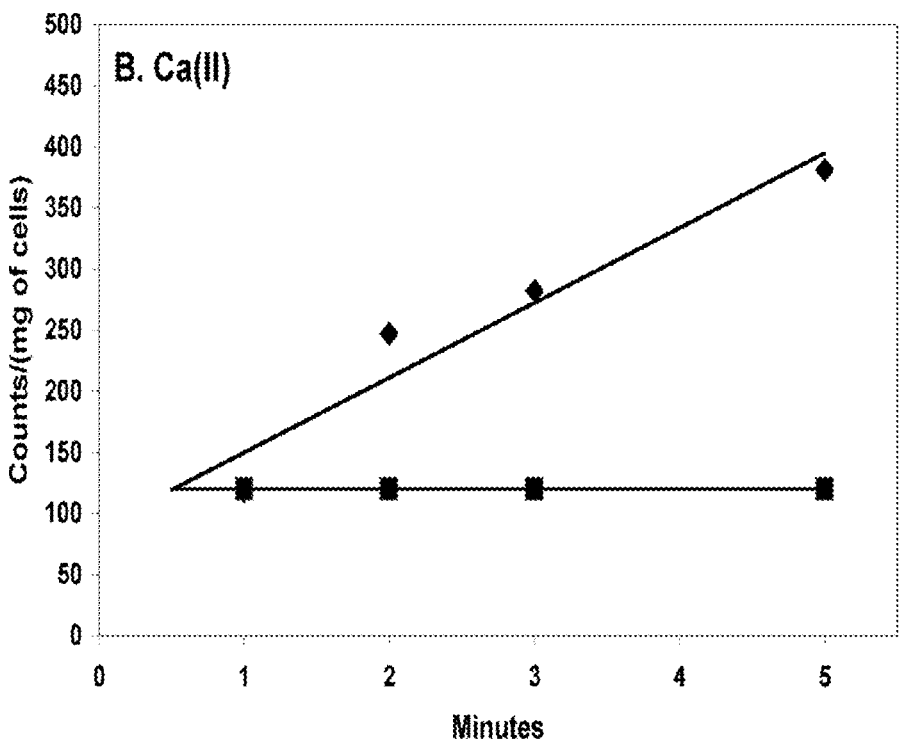
Figure 1C:
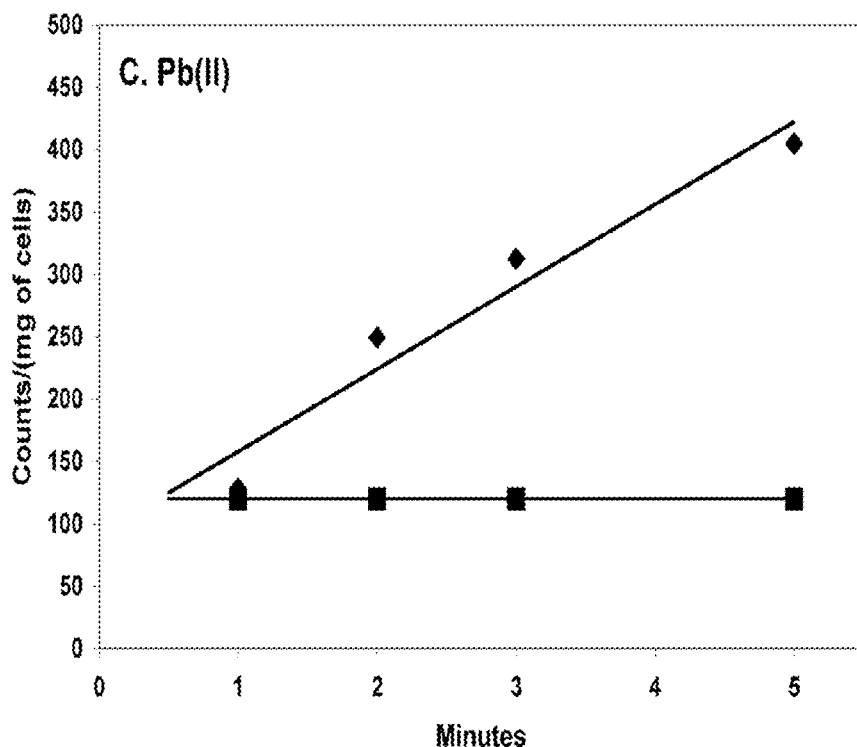
Figure 1D:
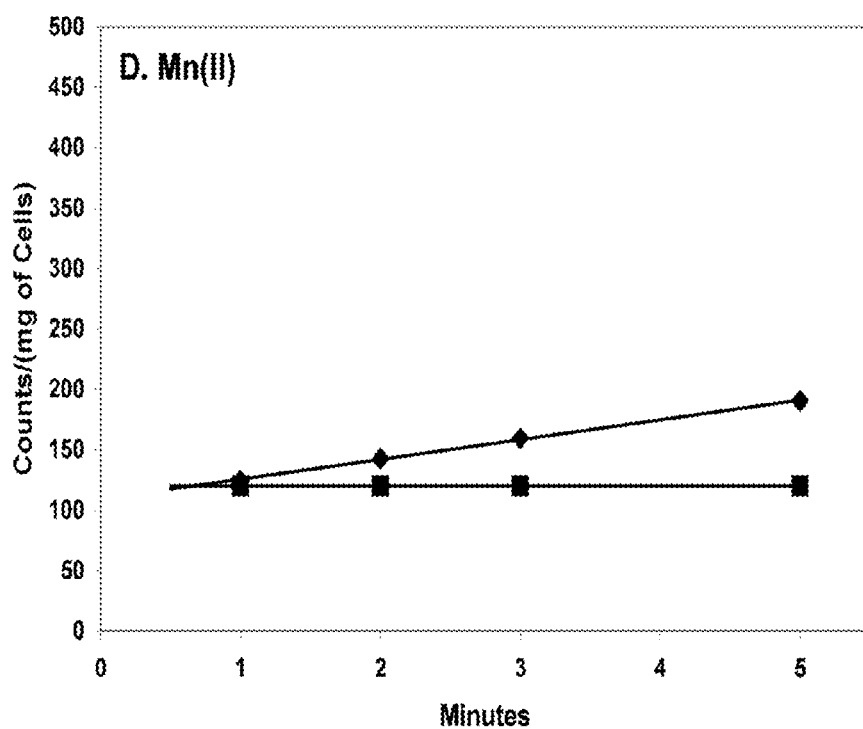
Figure 1E:
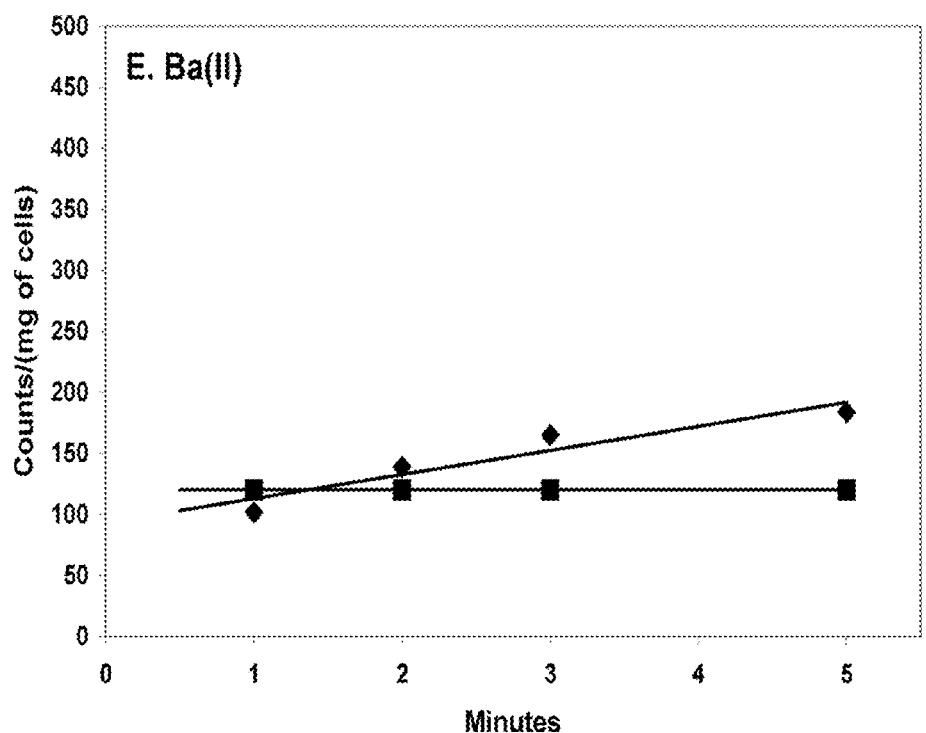
Figure 1F:
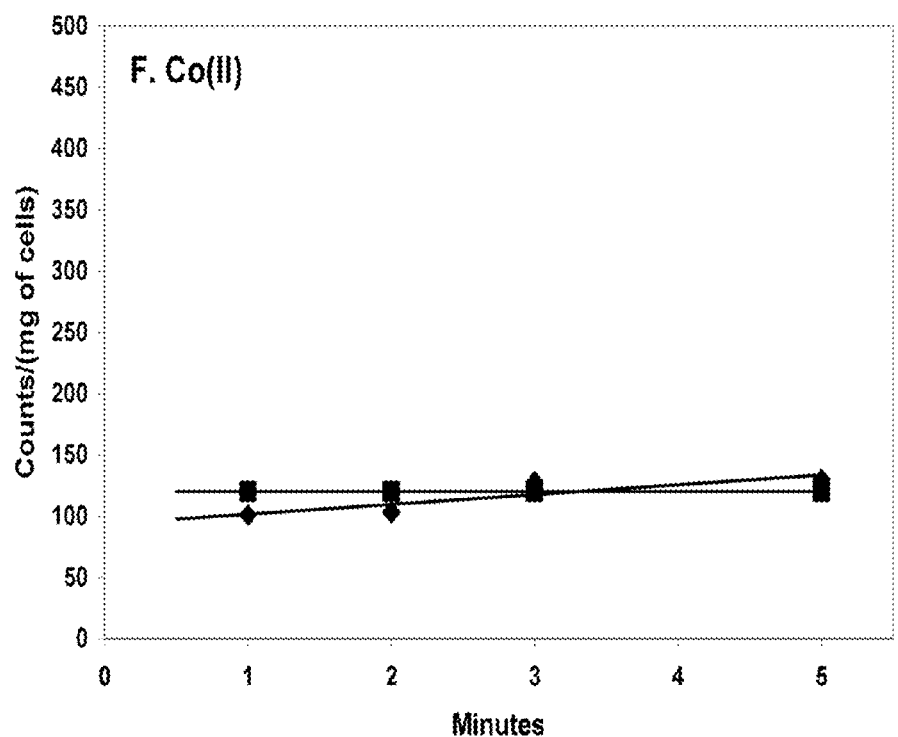
Figure 1G:
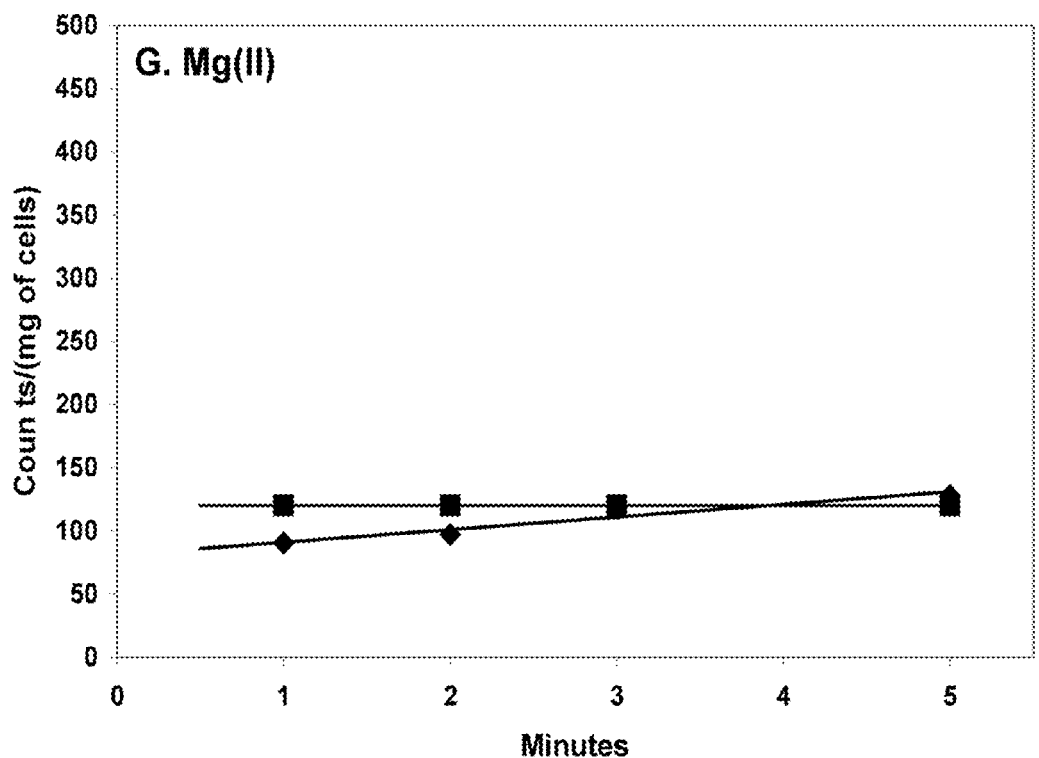
Figure 1H:
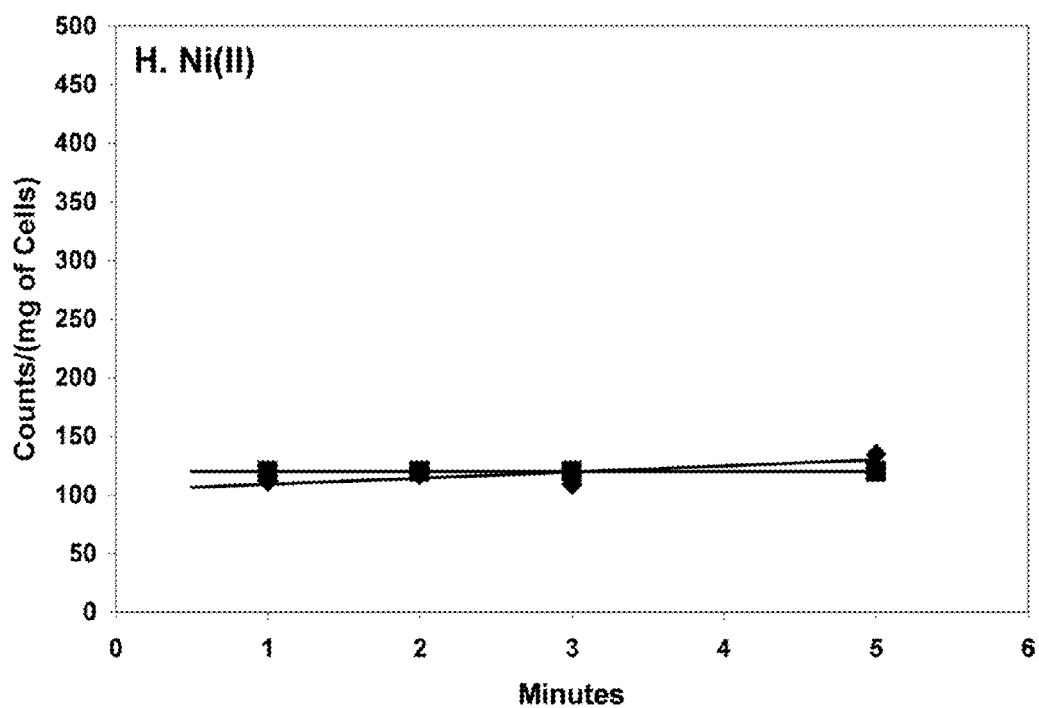

Various abbreviations and terms are used throughout to describe various aspects of the present invention. Below is a selected listing of certain of these abbreviations and terms.

As used herein, term "pathogenic bacteria" is meant to include any bacteria that causes infection or induces disease in a human or an animal, and that also uses a metal-citrate transporter to uptake iron. Examples of pathogenic bacteria include, but are not limited to, *Bacillus* spp., *Mycobacterium* spp., *Corynebacterium* spp., *Neisseria* spp., and *Burkholderia* spp. More particularly, pathogenic bacteria contemplated by the present invention can include, without limitation, such bacterial species as *Bacillus anthracis, Mycobacterium tuberculosis, Corynebacterium diphteriae, Neisseria meningitis, Neisseria gonorrhoeae, Burkholderia mallei, Burkholderia cepacia*, and *Burkholderia pseudomallei*. It is also recognized that certain bacterial strains that use metal-citrate transporters to uptake iron can be plant pathogenic bacteria, such as *Xanthomonas* spp., and more particularly *Xanthomonas campestris*.

As used herein, the abbreviations "$Cit_{Sc}$" and "Sccit" are used to denote the isolated metal-citrate transporter from *Streptomyces coelicolor* of the present invention.

The present invention takes advantage of the determination of the structural and functional characterization of the metal-citrate transporter of the present invention, which information was not known prior to the present invention. For example, in accordance with the present invention, it has been determined that $Cit_{Sc}$ is important in the uptake of iron by *S. coelicolor*.

Thus, in accordance with the present invention, treatments and preventative measures against pathogenic bacterial infection of humans and animals are provided. Such measures exploit the importance of iron limitation in blocking infection by pathogenic bacteria.

It is believed that $Cit_{Sc}$ is only the second example of a Gram-positive citrate transporter that preferentially uses ferric ions as a vital cofacter for transport. It is the first such member of the CitMHS to be successfully functionally characterized outside the native organism. It is also believed to be the first to show preferential metabolism of the transported $Fe^{3+}$-citrate species (over $Pb^{2+}$-citrate for example) when expressed heterologously. While not a pathogenic bacteria, *S. coelicolor* is a member of the Actinomycete family, which is related to bacteria such as *Neisseria meningitis*. Blocking uptake by pathogenic bacteria of iron citrate found in blood plasma of humans and animals would prevent such pathogenic bacteria from overcoming iron-based bacteriostasis.

In one aspect, the present invention provides an isolated antigen that is useful for developing, inter alia, vaccines against pathogenic bacteria of humans and animals. The isolated antigen can include an isolated metal-citrate transporter from *Streptomyces coelicolor*. The isolated antigen can also include an isolated immunogenic polypeptide fragment of said metal-citrate transporter, where the immunogenic fragment retains an antigenic activity of said metal-citrate transporter.

In one embodiment, the isolated antigen is a $Cit_{Sc}$ polypeptide having an amino acid sequence of SEQ ID NO:1, as follows:

```
Met Leu Thr Ile Leu Gly Phe Ala Met Ile Ala Thr Phe Leu Val Leu
1               5                   10                  15
Ile Met Met Lys Lys Met Ser Pro Ile Ala Ala Leu Val Leu Ile Pro
                20              25                  30
Ala Leu Phe Cys Val Leu Val Gly Lys Gly Ala His Leu Gly Asp Tyr
            35              40                  45
Val Ile Asp Gly Val Ser Ser Leu Ala Pro Thr Ala Ala Met Leu Met
        50              55              60
Phe Ala Ile Val Tyr Phe Gly Val Met Ile Asp Val Gly Leu Phe Asp
65                      70              75                      80
Pro Ile Val Arg Ala Ile Leu Lys Phe Cys Lys Ala Asp Pro Met Arg
                85              90                      95
Ile Val Val Gly Thr Ala Leu Leu Ala Ala Ile Val Ser Leu Asp Gly
            100             105             110
Asp Gly Ser Thr Thr Phe Met Ile Thr Val Ser Ala Met Tyr Pro Leu
        115             120             125
Tyr Lys Arg Leu Lys Met Ser Leu Val Val Met Thr Gly Val Ala Ala
        130             135             140
Met Ala Asn Gly Val Met Asn Thr Leu Pro Trp Gly Gly Pro Thr Ala
145             150             155             160
Arg Ala Ala Thr Ala Leu Lys Val Asp Ala Thr Asp Ile Phe Val Pro
                165             170             175
Met Ile Pro Ala Leu Ala Val Gly Leu Val Ala Val Val Val Leu Ala
            180             185             190
Tyr Val Leu Gly Leu Arg Glu Arg Arg Arg Leu Gly Thr Leu Ser Leu
        195             200             205
Asp Gly Ala Pro Glu Arg Glu Pro Glu Thr Glu Thr Val Leu Val Gly
        210             215             220
Ala Gly Ala Gly Thr Gly Ala Ala Gly Leu Ser Gly Ala Gly Ala Gly
```

-continued

```
                225                 230                 235                 240
Ala Gly Ala Gly Ala Ala Arg Gly Ala Ala Gly Gly Pro Gly Ala Ala
                245                 250                 255
Gly Asp Arg Asp Thr Gly Ala Gly Gly Glu Ser Asp Asp Phe Lys
                260                 265                 270
Gly Leu Asp Pro Asn Arg Pro Thr Leu Arg Pro Arg Leu Tyr Trp Phe
                275                 280                 285
Asn Ala Leu Leu Thr Leu Ala Leu Leu Thr Ala Met Ile Met Glu Leu
                290                 295                 300
Leu Pro Ile Pro Val Leu Phe Leu Ile Gly Ala Ala Leu Ala Leu Thr
305                 310                 315                 320
Val Asn Phe Pro His Ile Pro Asp Gln Lys Ala Arg Ile Ala Ala His
                325                 330                 335
Ala Asp Asn Val Leu Asn Val Ser Gly Met Val Phe Ala Ala Ala Val
                340                 345                 350
Phe Thr Gly Val Leu Thr Gly Thr Gly Met Val Asp His Met Ala Asn
                355                 360                 365
Trp Leu Val Asp Thr Ile Pro Asp Gly Met Gly Pro Gln Met Gly Leu
                370                 375                 380
Val Thr Gly Leu Leu Ser Leu Pro Leu Thr Tyr Phe Met Ser Asn Asp
385                 390                 395                 400
Gly Phe Tyr Phe Gly Val Leu Pro Val Leu Ala Glu Ala Gly Gln Ala
                405                 410                 415
His Gly Val Ser Thr Leu Glu Ile Ala Arg Ala Ser Ile Val Gly Gln
                420                 425                 430
Pro Leu His Met Ser Ser Pro Leu Val Pro Ala Val Tyr Val Leu Val
                435                 440                 445
Gly Met Ala Lys Val Glu Phe Gly Asp His Thr Arg Phe Val Val Lys
                450                 455                 460
Trp Ala Val Leu Thr Ser Leu Val Ile Leu Ala Ala Gly Ile Leu Phe
465                 470                 475                 480
Gly Ile Ile
```

In another embodiment, the isolated antigen is a polypeptide having an amino acid sequence that has at least 60%, 70%, 80%, 85%, 90%, 95%, or 99% sequence identity to the amino acid sequence of SEQ ID NO:1. In another embodiment, the isolated antigen is a polypeptide having an amino acid sequence that has at least 60%, 70%, 80%, 85%, 90%, 95%, or 99% sequence identity to the amino acid sequence of SEQ ID NO:1, and further includes at least one of the following amino acid residues of SEQ ID NO:1: D75, D80, D111, N151, R161, Q438, H435, K452, H458, R460, and/or $K_{464}$.

In a further embodiment, the isolated antigen can include a fragment having an antigenic amino acid sequence corresponding to any portion of the $Cit_{Sc}$ polypeptide that is expressed on the surface of a pathogenic bacterial cell. A suitable fragment can include, without limitation, an antigenic amino acid sequence derived from SEQ ID NO:1, where the antigenic amino acid sequence includes at least one of the following amino acid residues of SEQ ID NO:1: D75, D80, D111, N151, R161, Q438, H435, K452, H458, R460, and/or K464.

In yet another embodiment, the isolated antigen of the present invention is a metal-citrate transporter that is encoded by a nucleotide sequence of SEQ ID NO:2 or degenerate nucleotide sequences of SEQ ID NO:2, where SEQ ID NO:2 is as follows:

```
atgctgacca tcctcggctt cgccatgatc gcgaccttcc tggtcctgat catgatgaag    60
aagatgtcgc cgatcgcggc gctcgtgctg attcccgcgc tgttctgcgt gctcgtcggc   120
aagggcgccc atctcggcga ctacgtcatc gacggcgtgt ccagcctcgc ccccaccgcg   180
gcgatgctca tgttcgcgat cgtctacttc ggtgtgatga tcgacgtcgg gctcttcgac   240
ccgatcgtcc gggccatcct gaagttctgc aaggccgacc cgatgcgcat cgtcgtcggc   300
acggcgctgc tcgccgcgat cgtctcgctg gacggcgacg gctccaccac cttcatgatc   360
acggtctcgg cgatgtaccc gctgtacaag cggctgaaga tgagcctggt cgtgatgacc   420
```

-continued

```
ggcgtcgccg cgatggccaa cggcgtgatg aacacgctgc cctggggcgg ccccaccgcc    480
cgcgccgcca ccgcgctgaa ggtcgacgcc accgacatct tcgtcccgat gatcccggcc    540
ctggccgtgg gtctggtcgc ggtcgtcgtc ctggcgtacg tgctcggtct gcgcgagcgc    600
aggcggctgg gcacgctgtc gctggacggg gcgccggagc gggagccgga gaccgagacg    660
gtgctggtcg gtgcgggcgc gggtacgggg gcggccgggc tttccggtgc gggtgcgggt    720
gcgggtgcgg gtgcggctcg cggcgcggcg ggcggcccccg gtgcggcggg cgaccgggac    780
accggggccg gcggcgagtc cgacgacgac ttcaagggcc tcgacccgaa ccggcccacc    840
ctgcggccca ggctgtactg gttcaacgcg ctgctcaccc tcgcgctgct caccgccatg    900
atcatggagc tgctgccgat cccggtgctc ttcctgatcg gcgccgcgct cgccctcacc    960
gtcaacttcc cgcacatccc ggaccagaag gcccgcatcg cggcccacgc cgacaacgtc   1020
ctcaacgtct ccggcatggt cttcgccgcc gccgtcttca ccggcgtcct caccggcacc   1080
ggcatggtcg accacatggc caactggctg gtggacacca tccccgacgg catgggcccg   1140
cagatgggcc tggtcaccgg cctgctgagc ctgccgctga cgtacttcat gtcgaacgac   1200
ggcttctact tcggcgtcct gccggtgctc gccgaggccg gccaggcgca cggcgtgtcg   1260
acgctggaga tcgcccgcgc ctcgatcgtc ggccagccgc tgcacatgtc cagcccgctc   1320
gtcccggccg tgtacgtcct ggtcggcatg gccaaggtcg agttcggcga ccacacgcgg   1380
ttcgtggtga agtgggccgt cctgacgagt ctggtgatcc tcgcggcggg catcctgttc   1440
ggcatcatct ga                                                        1452
```

Thus, the present invention provides nucleic acids that encode the Cit$_{Sc}$ protein and fragments thereof of the present invention. Such nucleic acids include those degenerate sequences that encode the same proteins, as well as those nucleic acids that can selectively hybridize with the nucleic acids coding for the Cit$_{sc}$ protein and fragments thereof of the invention.

In another aspect, the present invention provides a pharmaceutical composition that includes the isolated antigen and a pharmaceutically acceptable carrier.

In another aspect, the present invention provides a vaccine for immunizing an individual against a disease associated with a pathogenic bacteria. The vaccine includes an immunogenic amount of the isolated antigen of the present invention and a pharmaceutically acceptable carrier. The vaccine of the present invention can be used to immunize individuals against diseases induced by pathogenic bacteria such as *Bacillus* spp., *Mycobacterium* spp., *Corynebacterium* spp., *Neisseria* spp., and *Burkholderia* spp. More particularly, such pathogenic bacteria can include, but are not limited to, *Bacillus anthracis, Mycobacterium tuberculosis, Corynebacterium diphteriae, Neisseria meningitis, Neisseria gonorrhoeae, Burkholderia mallei, Burkholderia cepacia,* and *Burkholderia pseudomallei.*

The present invention further provides an isolated antibody or antigen-binding fragment thereof that specifically binds with high affinity to the isolated antigen of the present invention. The antibody of the present invention is suitable for oral, parenteral, intravenous, subcutaneous, intranasal, or aerosolized administration in a human or animal. The antibody can be a polyclonal antibody or a monoclonal antibody. More particularly, the monoclonal antibody of the present invention can be of various types, including, without limitation, human monoclonal antibodies, chimeric monoclonal antibodies, a murine monoclonal antibodies, and a humanized monoclonal antibodies. Further, the monoclonal antibody can be a single chain monoclonal antibody.

In another aspect, the present invention provides a pharmaceutical composition that includes the antibody of the present invention and a pharmaceutically acceptable carrier. In one embodiment, the pharmaceutical composition can further include a physiologically acceptable antibiotic.

The present invention further provides an isolated antisera containing the antibody of the present invention.

In another aspect, the present invention provides a diagnostic kit that includes the antibody of the present invention and a detecting agent for detecting binding by that antibody. In one embodiment, the detecting agent can include a detectable label that is linked to the antibody.

In yet a further aspect, the present invention provides a method for immunizing an individual against a disease associated with a pathogenic bacteria. In this method, an individual is administered a pharmaceutically effective amount of the vaccine of the present invention, thereby immunizing the individual against a disease associated with a pathogenic bacteria.

In another aspect, the present invention provides a method for inhibiting pathogenic bacteria infection of an individual. This method involves administering to an individual a pharmaceutically effective amount of the vaccine according to the present invention under conditions effective to inhibit iron uptake of the pathogenic bacteria from blood serum of the individual, thereby inhibiting infection of the individual by the pathogenic bacteria.

In one aspect, the present invention provides a method of treating or preventing pathogenic infection of an individual. This method involves administering to an individual an effective amount of the antibody according to the present invention under conditions effective to inhibit iron uptake of the pathogenic bacteria from blood serum of the individual, thereby treating or preventing infection of the individual by the pathogenic bacteria.

The present invention further provides a method for detecting a pathogenic bacteria in a biological sample of an individual. This method involves collecting a biological sample from an individual and contacting the sample with the isolated antibody or antigen-binding fragment thereof of the present invention. A successful binding event between the isolated antibody or antigen-binding fragment thereof to at least one component of the sample is detected, where detection of the successful binding event indicates the presence of the pathogenic bacteria in the biological sample.

The present invention also provides a method for detecting the presence of a pathogenic bacteria on a surface. This method involves contacting the surface with the isolated antibody or antigen-binding fragment thereof of the present invention and detecting a successful binding event between the isolated antibody or antigen-binding fragment thereof to at least one component contained on the surface. Under this method, detection of the successful binding event indicates the presence of the pathogenic bacteria on the surface.

In another aspect, the present invention provides an isolated polynucleotide that encodes the antigen of the present invention.

In a further aspect, the present invention provides a vector that includes the isolated polynucleotide of the present invention. In one embodiment, the isolated polynucleotide is linked in sense-orientation to regulatory elements that enable transcription of the polynucleotide and translation of the protein encoded therein in a prokaryotic or a eukaryotic cell.

The present invention also provides a host cell transformed with the vector of the present invention.

The present invention further provides a method for producing a metal-citrate transporter antigen from *Streptomyces coelicolor*. This method involves culturing the host cell of the present invention under conditions effective to produce the antigen, and then recovering the antigen from the culture.

Provided below are more details on the various aspects of the present invention.

In accordance with the present invention, it has been determined that $Cit_{sc}$ is a previously unidentified metal-citrate transporter. Additionally, it has been determined or is believed that: (i) defined regions in $Cit_{sc}$ can be expressed as recombinant proteins to generate antibodies that block ligand binding; (ii) defined regions in $Cit_{sc}$ can therefore be used as vaccines; (iii) antibodies (polyclonal or monoclonal antibodies) can be generated against $Cit_{sc}$ that may interfere with the uptake of iron in pathogenic bacteria; and (iv) antibodies (polyclonal or monoclonal antibodies) can be raised against $Cit_{sc}$ that be used as therapies against pathogenic bacterial infections.

Accordingly, the present invention is directed to the $Cit_{sc}$ protein antigen. In addition, another aspect of the present invention is the provision of nucleic acids coding for these proteins, or nucleic acids that selectively hybridize to such sequences, as well as to monoclonal and polyclonal antibodies which recognize these proteins, and pharmaceutical compositions including the proteins or antibodies of the invention. The present invention is further directed to methods of prevention and treatment of a pathogenic bacterial infection using $Cit_{sc}$ or its homologues, nucleic acids coding for said proteins, or antibodies recognizing said proteins.

The use of polyclonal or monoclonal antibodies reacting with $Cit_{sc}$ constitutes a new strategy for the prevention and treatment of infections caused by pathogenic bacteria. An analogous strategy, using antibodies targeted to the pathogenic bacteria, has been effective in animal models for the treatment and prevention of infections caused by pathogenic bacteria. The $Cit_{sc}$ has been cloned, and can be expressed in *E. coli*, and protective monoclonal and polyclonal antibodies can be generated against it using the various conventional methods outlined below. $Cit_{sc}$ has been isolated and sequenced, both with regard to protein and nucleic acid sequences, and this information is provided herein.

In terms of methods of treating pathogenic bacterial diseases, infections caused by such pathogenic bacteria are generally difficult to treat, because some of these organisms are resistant to multiple antibiotics, and can form biofilms on the surface of the indwelling medical devices they infect. In accordance with the present invention, $Cit_{sc}$ or its homologues may be used as an immunogen to constitute an excellent preparation to develop therapies to treat and prevent pathogenic bacterial infections, because the evidence shows that metal-citrate transporters like $Cit_{sc}$ appear to be important in the uptake of iron by pathogenic bacteria. The advantage of using $Cit_{sc}$ and antibodies generated against $Cit_{sc}$ as a treatment strategy for the prevention of pathogenic bacterial infections is that the humanized antibodies can be effective and are not believed to cause secondary adverse reactions.

Thus, in one aspect, the present invention outlines how $Cit_{sc}$ can be used to generate effective polyclonal and monoclonal antibodies for the prevention and treatment of infections caused by pathogenic bacteria.

In accordance with the present invention, peptides or recombinant proteins of $Cit_{sc}$ or its homologues, or polypeptides that contain the active site or sites on $Cit_{sc}$, and thus are responsible for their extracellular matrix binding properties, are included in the invention along with the use of these peptides or recombinant proteins as means of preventing iron uptake by pathogenic bacteria in host tissues, blood serum, or the like from animals and/or humans.

As indicated above, antibodies in accordance with the present invention will be those antibodies capable of binding with the $Cit_{sc}$ protein or its homologues, and thus the present invention contemplates the generation of antibodies from these $Cit_{sc}$ proteins obtained using methods of generating an immune response from these proteins or from antigenic regions from these proteins. By "antibody" is meant any intact antibody molecule or fragments thereof that recognize antigen (e.g. Fab or F(ab')2 fragments) and can be of polyclonal or monoclonal type, and the antibodies in accordance with the invention will be capable of recognizing the $Cit_{sc}$ proteins of the invention and/or the specific antigenic epitopes from said proteins or other immunogenic regions. These antibodies will thus be effective in methods of diagnosing, monitoring, treating, or preventing infection from pathogenic bacteria that rely on iron uptake to induce infection and/or disease. By "epitope" is meant any antigenic determinant responsible for immunochemical binding with an antibody molecule. Epitopes usually reside within chemically active surface groupings of protein molecules (including amino acids and often also sugar side-chains) and have specific three-dimensional structural characteristics and specific charge characteristics. With reference to the proteins of the present invention, or epitopes and peptides as described herein, it is understood that such terms also include those proteins and peptides which differ from a naturally occurring or recombinant protein by the substitution, deletion and/or addition of one or more amino acids but which retains the ability to be recognized by an antibody raised against the entire protein. An example is a carrier/antigen fusion polypeptide of the whole antigen or an immunoreactive fragment thereof, where the antigen or fragment can be embedded within the carrier polypeptide or linked to the carrier polypeptide at either end.

Accordingly, in accordance with the present invention, isolated and/or purified antibodies can be generated from the $Cit_{sc}$ proteins of the present invention such as $Cit_{sc}$, or from particular epitopes. These antibodies may be monoclonal or polyclonal and may be generated using any suitable method to raise such antibodies such as would be well known in this art. The antibodies in accordance with the invention will be particularly useful in inhibiting the uptake of iron by pathogenic bacteria from human and/or animal sources, and in inhibiting the binding of pathogenic bacteria and metal-citrate transporters of such pathogenic bacteria to extracellular matrix components of the host cells, as well as in diagnosing, treating or preventing infections of pathogenic bacteria.

For example, with regard to polyclonal antibodies, these may be generated using a number of suitable methods well known to the practitioner of ordinary skill in the art and these methods generally involve the injection of the isolated and/or purified or recombinantly produced proteins (or their immunogenic active peptides or epitopes) into a suitable host in order to generate the polyclonal antibodies which can then be recovered from the host. For example, in accordance with the invention, an isolated and purified $Cit_{sc}$ protein or antigenic fragment thereof may be injected into rabbits in order to generate polyclonal antisera recognizing this protein.

In addition, monoclonal antibodies in accordance with the invention may be generated using a suitable hybridoma as would be readily understood by those of ordinary skill in the art. In the preferred process, a protein in accordance with the invention having a sequence as set forth below, which can thus be produced recombinantly using ordinary skill in the art, may be isolated and/or purified in any of a number of suitable ways commonly known in the art. In one suitable process, monoclonal antibodies may be generated from proteins isolated and purified as described above or by an addition of the protein with an adjuvant, and injecting the protein and/or mixture into BALB/c mice.

In general, the monoclonal antibodies of the invention may be produced using any of a variety of conventional methods, e.g., the method of Kohler and Milstein, Nature 256:495-497 (1975), or other suitable ways known in the field. In addition, it will be recognized that these monoclonals can be prepared in a number of forms, including chimeric, humanized, or human in addition to murine in ways that would be well known in this field. Still further, monoclonal antibodies may be prepared from a single chain, such as the light or heavy chains, and in addition may be prepared from active fragments of an antibody which retain the binding characteristics (e.g., specificity and/or affinity) of the whole antibody. By active fragments is meant an antibody fragment which has the same binding specificity as a complete antibody which binds to extracellular matrix binding proteins, and the term "antibody" as used herein is meant to include said fragments. Additionally, antisera prepared using monoclonal or polyclonal antibodies in accordance with the invention are also contemplated and may be prepared in a number of suitable ways as would be recognized by one skilled in the art.

In accordance with the present invention, antibodies are thus produced which are capable of recognizing and binding to the putative highly expressed $Cit_{sc}$ antigens as set forth above or epitopes and active regions from said proteins, and such antibodies can be utilized in many diagnostic and therapeutic applications such as the ones described herein.

In another aspect of the present invention, the isolated antibodies of the present invention, or the isolated proteins or epitopes as described above, may also be utilized in the development of vaccines for active and passive immunization against bacterial infections, as described further below. In the case of active vaccines, such vaccines are prepared by providing an immunogenic amount of the proteins of the invention or their active regions or epitopes as set forth above, and the active vaccine in accordance with the invention will thus comprise an immunogenic amount of the protein or peptide and will be administered to a human or animal in need of such a vaccine. The vaccine may also comprise a suitable, pharmaceutically acceptable vehicle, excipient or carrier which will be those known and commonly used in the vaccine arts. As referred to herein, an "immunogenic amount" of the antigen to be used in accordance with the present invention is intended to mean a nontoxic but sufficient amount of the agent, such that an immunogenic response will be elicited in the host so that the desired prophylactic or therapeutic effect is produced. Accordingly, the exact amount of the antigen that is required will vary from subject to subject, depending on the species, age, and general condition of the subject, the severity of the condition being treated, the particular carrier or adjuvant being used and its mode of administration, and the like. Similarly, the "immunogenic amount" of any such antigenic vaccine composition will vary based on the particular circumstances, and an appropriate immunogenic amount may be determined in each case of application by one of ordinary skill in the art using only routine experimentation. The dose should be adjusted to suit the individual to whom the composition is administered and will vary with age, weight and metabolism of the individual.

Further, when administered as pharmaceutical composition to a patient or used to coat medical devices or polymeric biomaterials in vitro and in vivo, the antibodies of the present invention may also be useful because these antibodies may be able to interfere with the ability of pathogenic bacteria to adhere to host cells and limit the extent and spread of the infection.

In addition, the antibody may be modified as necessary so that, in certain instances, it is less immunogenic in the patient to whom it is administered. For example, if the patient is a human, the antibody may be "humanized" by transplanting the complimentarily determining regions of the hybridoma-derived antibody into a human monoclonal antibody as described, e.g., by Jones et al., *Nature* 321:522-525 (1986) or Tempest et al. *Biotechnology* 9:266-273 (1991) or "veneered" by changing the surface exposed murine framework residues in the immunoglobulin variable regions to mimic a homologous human framework counterpart as described, e.g., by Padlan, *Molecular Imm.* 28:489-498 (1991), these references being incorporated herein by reference. Even further, under certain circumstances, it may be desirable to combine the monoclonal antibodies of the present invention with a suitable antibiotic when administered so as to further enhance the ability of the present compositions to fight or prevent infections.

In a preferred embodiment, the antibodies may also be used as a passive vaccine which will be useful in providing suitable antibodies to treat or prevent a pathogenic bacterial infection. As would be recognized by one skilled in this art, a vaccine may be packaged for administration in a number of suitable ways, such as by parenteral administration (i.e., intramuscular, intradermal or subcutaneous) or nasopharyngeal administration (i.e., intranasal). One such mode is where the vaccine is injected intramuscularly, e.g., into the deltoid muscle, however, the particular mode of administration will depend on the nature of the bacterial infection to be dealt with and the condition of the patient. The vaccine is preferably combined with a pharmaceutically acceptable vehicle, carrier or excipient to facilitate administration, and the carrier is usually water or a buffered saline, with or without a preservative. The vaccine may be lyophilized for resuspension at the time of administration or in solution.

The preferred dose for administration of an antibody composition in accordance with the present invention is that amount will be effective in preventing of treating a bacterial infection, and one would readily recognize that this amount will vary greatly depending on the nature of the infection and the condition of a patient. An "effective amount" of antibody or pharmaceutical agent to be used in accordance with the invention is intended to mean a nontoxic but sufficient amount of the agent, such that the desired prophylactic or therapeutic effect is produced. Accordingly, the exact amount of the antibody or a particular agent that is required will vary from subject to subject, depending on the species, age, and general condition of the subject, the severity of the condition being treated, the particular carrier or adjuvant being used and its mode of administration, and the like. Accordingly, the "effective amount" of any particular antibody composition will vary based on the particular circumstances, and an appropriate effective amount may be determined in each case of application by one of ordinary skill in the art using only routine experimentation. The dose should be adjusted to suit the individual to whom the composition is administered and will vary with age, weight and metabolism of the individual. The compositions may additionally contain stabilizers or pharmaceutically acceptable preservatives, such as thimerosal (ethyl(2-mercaptobenzoate-S)mercury sodium salt) (Sigma Chemical Company, St. Louis, Mo.).

In addition, the antibody compositions of the present invention and the vaccines as described above may also be administered with a suitable adjuvant in an amount effective to enhance the immunogenic response against the conjugate. For example, suitable adjuvants may include alum (aluminum phosphate or aluminum hydroxide), which is used widely in humans, and other adjuvants such as saponin and its purified component Quil A, Freund's complete adjuvant, and other adjuvants used in research and veterinary applications. Still other chemically defined preparations such as muramyl dipeptide, monophosphoryl lipid A, phospholipid conjugates such as those described by Goodman-Snitkoff et al. *J. Immunol.* 147:410-415 (1991) and incorporated by reference herein, encapsulation of the conjugate within a proteoliposome as described by Miller et al., *J. Exp. Med.* 176:1739-1744 (1992) and incorporated by reference herein, and encapsulation of the protein in lipid vesicles such as NOVASOME® lipid vesicles (Micro Vescular Systems, Inc., Nashua, N.H.) may also be useful.

Accordingly, the present invention provides polyclonal and monoclonal antibodies which recognize a highly expressed antigen from $Cit_{sc}$ which can bind to metal-citrate transporters in pathogenic bacteria so as to be useful in methods of treating, preventing or diagnosing pathogenic bacterial infections. The present invention thus contemplates these monoclonal antibodies, and other monoclonals recognizing the same epitopes of the specific monoclonals described herein. The present invention also contemplates proteins and antibodies which can be useful in methods of inhibiting adherence of pathogenic bacteria to host cells and thus treat or prevent a pathogenic bacterial infection when used in amounts effective to prevent or treat such infections.

As would be recognized by one skilled in the art, the proteins and antibodies of the present invention may also be formed into suitable pharmaceutical compositions for administration to a human or animal patient in order to treat or prevent an infection caused by pathogenic bacteria. Pharmaceutical compositions containing the proteins or antibodies of the present invention, or effective fragments thereof, e.g., antigen portions of the proteins, or effective portions of the antibodies such as fragments maintaining the binding properties of the whole antibody, may be formulated in combination with any suitable pharmaceutical vehicle, excipient or carrier that would commonly be used in this art, including such conventional materials for this purpose, e.g., saline, dextrose, water, glycerol, ethanol, other therapeutic compounds, and combinations thereof. As one skilled in this art would recognize, the particular vehicle, excipient or carrier used will vary depending on the patient and the patient's condition, and a variety of modes of administration would be suitable for the compositions of the invention, as would be recognized by one of ordinary skill in this art. Suitable methods of administration, of any pharmaceutical composition disclosed in this application include, but are not limited to, topical, oral, anal, vaginal, intravenous, intraperitoneal, intramuscular, subcutaneous, intranasal and intradermal administration.

If topical administration is desired, the composition may be formulated as needed in a suitable form, e.g., an ointment, cream, gel, lotion, drops (such as eye drops and ear drops), or solution (such as mouthwash). Wound or surgical dressings, sutures and aerosols may be impregnated with the composition. The composition may contain conventional additives, such as preservatives, solvents to promote penetration, and emollients. Topical formulations may also contain conventional carriers such as cream or ointment bases, ethanol, or oleyl alcohol.

Additional forms of antibody or protein compositions are disclosed in other patents relating to pathogenic bacterial proteins which will generally be applicable to the present invention as well, and these patents include U.S. Pat. Nos. 7,045,131; 6,994,855; 6,979,446; 6,841,154; 6,703,025; 6,692,739; 6,685,943; 6,680,195; 6,635,473; 6,288,214; 6,177,084; and 6,008,341, all of said patents incorporated herein by reference.

The antibody compositions of the present invention will thus be useful for interfering with, modulating, or inhibiting uptake of iron by pathogenic bacteria, as well as interfering with, modulating, or inhibiting binding interactions of pathogenic bacteria on host cells and tissues, and will thus have particular applicability in developing compositions and methods of preventing or treating pathogenic bacterial infection, and in inhibiting infection by pathogenic bacteria to host tissue and/or cells.

In accordance with the present invention, methods are provided for preventing or treating a pathogenic bacterial infection which include administering an effective amount of the antibody of the present invention as described above in amounts effective to treat or prevent the infection. In addition, these antibodies will be useful in inhibiting iron uptake of bacterial pathogens, and/or in inhibiting pathogenic bacteria binding to the extracellular matrix of the host, and in reducing or eliminating the adherence of pathogenic bacteria on host cells or on other surfaces, e.g., medical equipment, implants or prosthetics.

Accordingly, in accordance with the invention, administration of the antibodies of the present invention in any of the conventional ways described above (e.g., topical, parenteral, intramuscular, etc.), and will thus provide an extremely useful method of treating or preventing pathogenic bacterial infections in human or animal patients. By effective amount is meant that level of use, such as of an antibody titer, that will be sufficient to inhibit uptake of iron by pathogenic bacteria and thus be useful in the treatment or prevention of a pathogenic bacterial infection. As would be recognized by one of ordinary skill in this art, the level of antibody titer needed to be effective in treating or preventing pathogenic bacterial infection will vary depending on the nature and condition of the patient, and/or the severity of the pre-existing pathogenic bacterial infection.

In addition to the use of antibodies of the present invention to treat or prevent pathogenic bacterial infections as described above, the present invention contemplates the use of these antibodies in a variety of ways, including the detection of the presence of pathogenic bacteria to diagnose an infection, whether in a patient or on medical equipment, implants or prosthetics which may also become infected. In accordance with the invention, a preferred method of detecting the presence of pathogenic bacterial infections involves the steps of obtaining a sample suspected of being infected by one or more pathogenic bacteria species or strains, such as a sample taken from an individual, for example, from one's blood, saliva, tissues, bone, muscle, cartilage, or skin. The cells can then be lysed, and the DNA extracted, precipitated and amplified. Following isolation of the sample, diagnostic assays utilizing the antibodies of the present invention may be carried out to detect the presence of the pathogenic bacteria, and such assay techniques for determining such presence in a sample are well known to those skilled in the art and include methods such as radioimmunoassay, Western blot analysis and ELISA assays. In general, in accordance with the present invention, a method of diagnosing a pathogenic bacterial infection is contemplated wherein a sample suspected of being infected with pathogenic bacterial infection has added to it the antibody in accordance with the present invention, and such an infection is indicated by antibody binding to the proteins in the sample.

Accordingly, antibodies in accordance with the invention may be used for the specific detection or diagnosis of pathogenic bacteria proteins, for the prevention of infection from pathogenic bacteria, for the treatment of an ongoing infection, or for use as research tools. The term "antibodies" as used herein includes monoclonal, polyclonal, chimeric, single chain, bispecific, simonized, and humanized or primatized antibodies as well as Fab fragments, such as those fragments which maintain the binding specificity of the antibodies to the $Cit_{sc}$ proteins, including the products of an Fab immunoglobulin expression library.

When so desired for medical or research purposes, any of the above described antibodies may be labeled directly with a detectable label for identification and quantification of pathogenic bacteria. Labels for use in immunoassays are generally known to those skilled in the art and include enzymes, radioisotopes, and fluorescent, luminescent and chromogenic substances, including colored particles such as colloidal gold or latex beads. Suitable immunoassays include enzyme-linked immunosorbent assays (ELISA).

Alternatively, the antibody may be labeled indirectly by reaction with labeled substances that have an affinity for immunoglobulin. The antibody may be conjugated with a second substance and detected with a labeled third substance having an affinity for the second substance conjugated to the antibody. For example, the antibody may be conjugated to biotin and the antibody-biotin conjugate detected using labeled avidin or streptavidin. Similarly, the antibody may be conjugated to a hapten and the antibody-hapten conjugate detected using labeled anti-hapten antibody. These and other methods of labeling antibodies and assay conjugates are well known to those skilled in the art.

Antibodies as described above may also be used in production facilities or laboratories to isolate additional quantities of the proteins, such as by affinity chromatography. For example, the antibodies of the invention may also be utilized to isolate additional amounts of the $Cit_{sc}$ proteins or their active fragments.

The isolated antibodies of the present invention, or active fragments thereof, may also be utilized in the development of vaccines for passive immunization against pathogenic bacterial infections. Further, when administered as pharmaceutical composition to a wound or used to coat medical devices or polymeric biomaterials in vitro and in vivo, the antibodies of the present invention, may be useful in those cases where there is a previous pathogenic bacterial infection because of the ability of this antibody to further restrict and inhibit pathogenic bacteria binding to host cells and thus limit the extent and spread of the infection. In addition, the antibody may be modified as necessary so that, in certain instances, it is less immunogenic in the patient to whom it is administered. For example, if the patient is a human, the antibody may be "humanized" by transplanting the complimentarily determining regions (CDRs) of the hybridoma-derived antibody into a human monoclonal antibody as described, e.g., by Jones et al., *Nature* 321:522-525 (1986) or Tempest et al. *Biotechnology* 9:266-273 (1991) or "veneered" by changing the surface exposed murine framework residues in the immunoglobulin variable regions to mimic a homologous human framework counterpart as described, e.g., by Padlan, *Molecular Imm.* 28:489-498 (1991) and U.S. Pat. No. 6,797,492, all of these references incorporated herein by reference. Even further, when so desired, the monoclonal antibodies of the present invention may be administered in conjunction with a suitable antibiotic to further enhance the ability of the present compositions to fight bacterial infections.

As indicated above, pathogenic bacterial infections are not only a problem with patients but also may affect medical devices, implants and prosthetics, and thus the present invention can be utilized to protect these devices from pathogenic bacterial infection as well, e.g., by coating these devices with the compositions of the present invention. Medical devices or polymeric biomaterials to be coated with the antibody compositions described herein include, but are not limited to, staples, sutures, replacement heart valves, cardiac assist devices, hard and soft contact lenses, intraocular lens implants (anterior chamber or posterior chamber), other implants such as corneal inlays, kerato-prostheses, vascular stents, epikeratophalia devices, glaucoma shunts, retinal staples, scleral buckles, dental prostheses, thyroplastic devices, laryngoplastic devices, vascular grafts, soft and hard tissue prostheses including, but not limited to, pumps, electrical devices including stimulators and recorders, auditory prostheses, pacemakers, artificial larynx, dental implants, mammary implants, other implants, cranio/facial tendons, artificial joints, tendons, ligaments, menisci, and disks, artificial bones, artificial organs including artificial pancreas, artificial hearts, artificial limbs, and heart valves; stents, wires, guide wires, intravenous and central venous catheters, laser and balloon angioplasty devices, vascular and heart devices (tubes, catheters, balloons), ventricular assists, blood dialysis components, blood oxygenators, urethreuretheral/urinary devices (Foley catheters, stents, tubes and balloons), airway catheters (endrotracheal and tracheotomy tubes and cuffs), enteral feeding tubes (including nasogastric, intragastric and jejunal tubes), wound drainage tubes, tubes used to drain the body cavities such as the pleural, peritoneal, cranial, and pericardial cavities, blood bags, test tubes, blood collection tubes, vacutainers, syringes, needles, pipettes, pipette tips, and blood tubing.

It will be understood by those skilled in the art that the term "coated" or "coating," as used herein, means to apply the antibody or pharmaceutical composition derived therefrom, to a surface of the device, preferably an outer surface that would be exposed to pathogenic bacterial infection. The surface of the device need not be entirely covered by the protein, antibody or active fragment.

In a preferred embodiment, the antibodies may also be used as a passive vaccine which will be useful in providing suitable antibodies to treat or prevent a pathogenic bacterial infection. As would be recognized by one skilled in this art, a vaccine may be packaged for administration in a number of suitable ways, such as by parenteral administration (i.e., intramuscular, intradermal or subcutaneous) or nasopharyngeal administration (i.e., intranasal). One such mode is where the vaccine is injected intramuscularly, e.g., into the deltoid muscle, however, the particular mode of administration will depend on the nature of the bacterial infection to be dealt with and the condition of the patient. The vaccine is preferably combined with a pharmaceutically acceptable carrier to facilitate administration, and the carrier is usually water or a buffered saline, with or without a preservative. The vaccine may be lyophilized for resuspension at the time of administration or in solution.

The preferred dose for administration of an antibody composition in accordance with the present invention is that amount will be effective in preventing of treating a pathogenic bacterial infection, and one would readily recognize that this amount will vary greatly depending on the nature of the infection and the condition of a patient. As indicated above, an "effective amount" of antibody or pharmaceutical agent to be used in accordance with the invention is intended to mean a nontoxic but sufficient amount of the agent, such that the desired prophylactic or therapeutic effect is produced. As will be pointed out below, the exact amount of the antibody or a particular agent that is required will vary from subject to subject, depending on the species, age, and general condition of the subject, the severity of the condition being treated, the particular carrier or adjuvant being used and its mode of administration, and the like. Accordingly, the "effective amount" of any particular antibody composition will vary based on the particular circumstances, and an appropriate effective amount may be determined in each case of application by one of ordinary skill in the art using only routine experimentation. The dose should be adjusted to suit the individual to whom the composition is administered and will vary with age, weight and metabolism of the individual. The compositions may additionally contain stabilizers or pharmaceutically acceptable preservatives, such as thimerosal (ethyl (2-mercaptobenzoate-S)mercury sodium salt) (Sigma Chemical Company, St. Louis, Mo.).

When used with suitable labels or other appropriate detectable biomolecule or chemicals, the monoclonal antibodies described herein are useful for purposes such as in vivo and in vitro diagnosis of pathogenic bacterial infections or detection of pathogenic bacteria. Laboratory research may also be facilitated through use of such antibodies. Various types of labels and methods of conjugating the labels to the antibodies of the invention are well known to those skilled in the art, such as the ones set forth below.

For example, the antibody can be conjugated (directly or via chelation) to a radiolabel such as, but not restricted to, $^{32}P$, $^{3}H$, $^{14}C$, $^{35}S$, $^{125}I$, or $^{131}I$. Detection of a label can be by methods such as scintillation counting, gamma ray spectrometry or autoradiography. Bioluminescent labels, such as derivatives of firefly luciferin, are also useful. The bioluminescent substance is covalently bound to the protein by conventional methods, and the labeled protein is detected when an enzyme, such as luciferase, catalyzes a reaction with ATP causing the bioluminescent molecule to emit photons of light. Fluorogens may also be used to label proteins. Examples of fluorogens include fluorescein and derivatives, phycoerythrin, allo-phycocyanin, phycocyanin, rhodamine, and Texas Red. The fluorogens are generally detected by a fluorescence detector.

The location of a ligand in cells can be determined by labeling an antibody as described above and detecting the label in accordance with methods well known to those skilled in the art, such as immunofluorescence microscopy using procedures such as those described by Warren et al. (*Mol. Cell. Biol.*, 7: 1326-1337, 1987).

As indicated above, the antibodies of the present invention, or active portions or fragments thereof, are particularly useful for interfering with the uptake of iron by pathogenic bacteria, and may also be effective in interfering with the initial physical interaction between a bacterial pathogen responsible for infection and a mammalian host, such as the adhesion of the bacteria to mammalian extracellular matrix proteins, and this interference with physical interaction may be useful both in treating patients and in preventing or reducing bacteria infection on in-dwelling medical devices to make them safer for use.

In another embodiment of the present invention, a kit which may be useful in isolating and identifying pathogenic bacteria and infection is provided which comprises the antibodies of the present invention in a suitable form, such as lyophilized in a single vessel which then becomes active by addition of an aqueous sample suspected of containing the pathogenic bacteria. Such a kit will typically include a suitable container for housing the antibodies in a suitable form along with a suitable immunodetection reagent which will allow identification of complexes binding to the antibodies of the invention. For example, the immunodetection reagent may comprise a suitable detectable signal or label, such as a biotin or enzyme that produces a detectable color, etc., which normally may be linked to the antibody or which can be utilized in other suitable ways so as to provide a detectable result when the antibody binds to the antigen.

As indicated above, the proteins and antibodies of the invention may also be formed into suitable pharmaceutical compositions for administration to a human or animal patient in order to treat or prevent a pathogenic bacterial infection. Pharmaceutical compositions containing the proteins or antibodies of the present invention as defined and described above may be formulated in combination with any suitable pharmaceutical vehicle, excipient or carrier that would commonly be used in this art, including such as saline, dextrose, water, glycerol, ethanol, other therapeutic compounds, and combinations thereof. As one skilled in this art would recognize, the particular vehicle, excipient or carrier used will vary depending on the patient and the patient's condition, and a variety of modes of administration would be suitable for the compositions of the invention, as would be recognized by one of ordinary skill in this art. Suitable methods of administration of any pharmaceutical composition disclosed in this application include, but are not limited to, topical, oral, anal, vaginal, intravenous, intraperitoneal, intramuscular, subcutaneous, intranasal and intradermal administration.

For topical administration, the composition may be formulated in the form of an ointment, cream, gel, lotion, drops (such as eye drops and ear drops), or solution (such as mouthwash). Wound or surgical dressings, sutures and aerosols may be impregnated with the composition. The composition may contain conventional additives, such as preservatives, solvents to promote penetration, and emollients. Topical formulations may also contain conventional carriers such as cream or ointment bases, ethanol, or oleyl alcohol.

Additional forms of compositions, and other information concerning compositions, methods and applications with regard to other microbial surface proteins and peptides that can be used in the present invention can be found in other patent references relating to pathogenic bacteria proteins, including, for example, in U.S. Pat. No. 6,288,214 (Hook et al.), incorporated herein by reference.

The compositions of the present invention will thus be useful for interfering with, modulating, or inhibiting iron uptake by pathogenic bacteria, and may further be useful for interfering with, modulating, or inhibiting binding interactions by pathogenic bacteria. Accordingly, the present invention will have particular applicability in developing compositions and methods of preventing or treating pathogenic bacterial infections, and in inhibiting infection, binding, and spreading of bacteria to host cells.

In accordance with the present invention, the detection of pathogenic bacteria present in a biological fluid (e.g. blood, serum, plasma, saliva, urine, cerebrospinal fluid, genitourinary tract) or other biological material (e.g., tissues, bone, muscle, cartilage, or skin) can constitute a method for the diagnosis of acute or chronic infections caused by pathogenic bacteria. Because the antibodies as set forth herein can recognize the epitopes found in pathogenic bacteria, these antibodies can be used in assays to allow the diagnosis of an pathogenic bacteria associated and disease conditions. Either monoclonal antibodies or polyclonal antibodies could be used in the assay, and in the case of the monoclonals such as those referred to above. The detected antigens identified by use of the present assays can be detected by a number of conventional means, including Western immunoblot and other similar tests.

With regard to the assays of the present invention, these assays may use the antibodies of the invention in labeled form, and all well-known methods of labeling antibodies are contemplated, including without limitation enzymatic conjugates, direct labeling with dye, radioisotopes, fluorescence, or particulate labels, such as liposome, latex, polystyrene, and colloid metals or nonmetals. Multiple antibody assay systems, such as antigen capture sandwich assays, are also within the scope of this invention. Further, competitive immunoassays involving labeled protein or assays using the labeled protein to detect serum antibodies are also contemplated forms of the diagnostic assays of the present invention. Beyond diagnostic assays which occur in solution, assays which involve immobilized antibody or protein are also considered within the scope of the invention (see, for example, Miles et al., Lancet 2:492, 1968; Berry et al., J. Virol. Met. 34:91-100, 1991; Engvall et al., G. Immunochemistry, 8:871, 1971, Tom, Liposomes and Immunology, Elsevier/North Holland, New York, N.Y., 1980; Gribnau et al., J. of Chromatogr. 376:175-89, 1986 and all references cited therein). Examples of the types of labels which can be used in the present invention include, but are not limited to, enzymes, radioisotopes, fluorescent compounds, chemiluminescent compounds, bioluminescent compounds, particulates, and metal chelates. Those of ordinary skill in the art will know of other suitable labels for binding to the monoclonal or polyclonal antibody (or to an antigen) or will be able to ascertain the same by the use of routine experimentation. Furthermore, the binding of these labels to the monoclonal or polyclonal antibody (or antigen) can be accomplished using standard techniques commonly known to those of ordinary skill in the art.

One of the ways in which an assay reagent (generally, a monoclonal antibody, polyclonal antibody or antigen) of the present invention can be detectably labeled is by linking the monoclonal antibody, polyclonal antibody, or antigen to an enzyme. This enzyme, in turn, when later exposed to its substrate, will react with the substrate in such a manner as to produce a chemical moiety which can be detected as, for example, by spectrophotometric or fluorometric means. Examples of enzymes which can be used to detectably label the reagents of the present invention include malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase.

The presence of the detectably labeled reagent of the present invention can also be detected by labeling the reagent with a radioactive isotope which can then be determined by such means as the use of a gamma counter or a scintillation counter. Isotopes which are particularly useful for the purpose of the present invention are $^{3}H$, $^{125}I$, $^{32}P$, $^{35}S$, $^{14}C$, $^{51}Cr$, $^{36}Cl$, $^{57}CO$, $^{58}CO$, $^{59}Fe$ and $^{75}Se$. It is also possible to detect the binding of the detectably labeled reagent of the present invention by labeling the monoclonal or polyclonal antibody with a fluorescent compound. When the fluorescently labeled reagent is exposed to light of the proper wave length, its presence can then be detected due to the fluorescence of the dye. Among the most commonly used fluorescent labeling compounds are fluorescein isothiocyanate, rhodamine, phycoerythrin, phycocyanin, allophycocyanin, o-phthaldehyde and fluorescamine. The reagents of the present invention also can be detectably labeled by coupling it to a chemiluminescent compound. The presence of the chemiluminescent-tagged reagent is then determined by detecting the presence of luminescence that arises during the course of the chemical reaction. Examples of particularly useful chemiluminescent labeling compounds are luminol, isoluminol, theromatic acridinium ester, imidazole, acridinium salt and oxalate ester. Likewise, a bioluminescent compound may be used to label the reagent of the present invention. Bioluminescence is a type of chemiluminescence found in biological systems in which a catalytic protein increases the efficiency of the chemiluminescent reaction. The presence of a bioluminescent reagent is determined by detecting the presence of luminescence. Important bioluminescent compounds for purposes of labeling are luciferin, luciferase and aequorin.

Another technique that may also result in greater sensitivity when used in conjunction with the present invention consists of coupling the monoclonal or polyclonal antibody of the present invention to low molecular weight haptens. The haptens can then be specifically detected by means of a second reaction. For example, it is common to use such haptens as biotin (reacting with avidin) or dinitrophenol, pyridoxal and fluorescamine (reacting with specific antihapten antibodies) in this manner. Any biological sample containing the detectable yet unknown amount of a $Cit_{sc}$ antigen can be used in the assay. Normally, the sample is preferably a liquid, such as, for example, urine, saliva, cerebrospinal fluid, blood, serum and the like, or a solid or semi-solid, such as, for example, tissue, feces and the like.

The diagnostic assay of the present invention includes kit forms of such an assay. This kit would include antibodies as described above (raised against whole proteins or active immunoreactive fragments or immunogenic analogs thereof) which can be optionally immobilized, as well as any necessary reagents and equipment to prepare the biological sample for and to conduct analysis, e.g. preservatives, reaction media such as nontoxic buffers, microtiter plates, micropipettes, etc. The reagent (Abs and/or antigens) can be lyophilized or cryopreserved. As described above, depending on the assay format, the antibodies can be labeled, or the kit can further comprise labeled proteins, fragments or analogs thereof containing the relevant epitopes so as to enable the detection of antibodies to $Cit_{sc}$ proteins in biological fluids and tissues. By analog is meant a protein or peptide which may differs from its naturally occurring or recombinant counterpart by the substitution, deletion and/or addition of one or more amino acids but which retains the ability to be recognized by an antibody raised against the entire protein. An example is a carrier/antigen fusion polypeptide of the whole antigen or an immunoreactive fragment thereof, where the antigen or fragment can be embedded within the carrier polypeptide or linked to the carrier polypeptide at either end. Accordingly, antibodies in accordance with the invention may also recognize such analogs. The types of immunoassays that can be incorporated in kit form are many. Typical examples of some of the immunoassays that can utilize the antibodies of the invention are radioimmunoassays (RIA) and immunometric, or sandwich, immunoassays.

"Immunometric assay" or "sandwich immunoassay" are meant to include simultaneous sandwich, forward sandwich and reverse sandwich immunoassays. These terms are well understood by those skilled in the art. Those of skill will also appreciate that the monoclonal antibodies, polyclonal antibodies and/or antigens of the present invention will be useful in other variations and forms of immunoassays which are presently known or which may be developed in the future. These are intended to be included within the scope of the present invention. In a forward sandwich immunoassay, a sample is first incubated with a solid phase immunoabsorbent containing monoclonal or polyclonal antibody(ies) against the antigen. Incubation is continued for a period of time sufficient to allow the antigen in the sample to bind to the immobilized antibody in the solid phase. After the first incubation, the solid phase immunoabsorbent is separated from the incubation mixture and washed to remove excess antigen and other interfering substances, such as non-specific binding proteins, which also may be present in the sample. Solid phase immunoabsorbent containing antigen bound to the immobilized antibody is subsequently incubated for a second time with soluble labeled antibody or antibodies. After the second incubation, another wash is performed to remove unbound labeled antibody(ies) from the solid phase immunoabsorbent and removing non-specifically bound labeled antibody(ies). Labeled antibody(ies) bound to the solid phase immunoabsorbent is then detected and the amount of labeled antibody detected serves as a direct measure of the amount of antigen present in the original sample.

Alternatively, labeled antibody which is not associated with the immunoabsorbent complex can also be detected, in which case the measure is in inverse proportion to the amount of antigen present in the sample. Forward sandwich assays are described, for example, in U.S. Pat. Nos. 3,867,517; 4,012,294 and 4,376,110, incorporated herein by reference. In carrying out forward immunometric assays, the process may comprise, in more detail: (a) first forming a mixture of the sample with the solid phase bound antibody(ies) and incubating the mixture for a time and under conditions sufficient to allow antigen in the sample to bind to the solid phase bound antibody(ies); (b) adding to the mixture after said incubation of step (a) the detectably labeled antibody or antibodies and incubating the new resulting mixture for a time and under conditions sufficient to allow the labeled antibody to bind to the antigen-antibody complex on the solid phase immunoabsorbent; (c) separating the solid phase immunoabsorbent from the mixture after the incubation in step (b); and (d) detecting either the labeled antibody or antibodies bound to the antigen-antibody complex on the solid phase immunoabsorbent or detecting the antibody not associated therewith.

In a reverse sandwich assay, the sample is initially incubated with labeled antibody(ies), after which the solid phase immunoabsorbent containing multiple immobilized antibodies is added thereto, and a second incubation is carried out. The initial washing step of a forward sandwich assay is not required, although a wash is performed after the second incubation. Reverse sandwich assays have been described, for example, in U.S. Pat. Nos. 4,098,876 and 4,376,110. In carrying out reverse immunometric assays, the process may comprise, in more detail: (a) first forming a mixture of the sample with the soluble detectably labeled antibody for a time and under conditions sufficient to allow antigen in the sample to bind to the labeled antibody; (b) adding to the mixture after the incubation of step (a) the solid phase bound antibodies and incubating the new resulting mixture for a time and under conditions sufficient to allow antigen bound to the labeled antibody to bind to the solid phase antibodies; (c) separating the solid phase immunoabsorbent from the incubating mixture after the incubation in step (b); and (d) detecting either the labeled antibody bound to the solid phase immunoabsorbent or detecting the labeled antibody not associated therewith.

EXAMPLES

The following examples are intended to illustrate particular embodiments of the present invention, but are by no means intended to limit the scope of the present invention. Certain of the Examples presented herein below include experimental data performed by the inventor and published as Joshua J. Lensbouer, Ami Patel, Joseph P. Sirianni, and Robert P. Doyle, "Functional Characterization and Metal Ion Specificity of the Metal-Citrate Complex Transporter from *Streptomyces coelicolor*," J. Bacteriol. 190(16):5616-5623 (August 2008) (E-Published Jun. 13, 2008), the entire disclosure of which is hereby incorporated by reference in its entirety.

Example 1

Functional Characterization and Metal Ion Specificity of the Metal-Citrate Complex Transporter from *Streptomyces coelicolor*

Secondary transporters of citrate in complex with metal ions belong to the bacterial CitMHS family, about which little is known. The transport of metal-citrate complexes in *Streptomyces coelicolor* has been investigated. The best cofactor for citrate uptake in *Streptomyces coelicolor* is $Fe^{3+}$ but uptake was also noted for $Ca^{2+}$, $Pb^{2+}$, $Ba^{2+}$ and $Mn^{2+}$. Uptake was not observed with $Mg^{2+}$, $Ni^{2+}$ or $Co^{2+}$ cofactors. The transportation of iron- and calcium-citrate makes this system unique among the CitMHS family members reported to date. No complementary uptake akin to that observed for the CitH ($Ca^{2+}$, $Ba^{2+}$, $Sr^{2+}$) and CitM ($Mg^{2+}$, $Ni^{2+}$, $Mn^{2+}$, $Co^{2+}$, $Zn^{2+}$) systems of *Bacillus subtilis* was noted. Competitive experiments using EGTA confirmed metal-citrate complex formation promoted citrate uptake. Uptake of free citrate was not observed. The open reading frame postulated as being responsible for the metal-citrate transport observed in *Streptomyces coelicolor* was cloned and overexpressed in *E. coli*, in strains with the primary $Fe^{3+}$-citrate transport system (fecABCDE) removed. Functional expression was successful with uptake of $Ca^{2+}$-citrate, $Fe^{3+}$-citrate and $Pb^{2+}$-citrate observed. No free citrate transport was observed in IPTG induced or uninduced *E. coli*. Metabolism of the $Fe^{3+}$-citrate and $Ca^{2+}$-citrate complex was observed, but not the $Pb^{2+}$-citrate complex. Rationalization is based on the difference in metal-complex coordination upon binding of the metal by citrate.

Example 2

Bacterial Strains and Growth Conditions

*Streptomyces coelicolor* A3(2) was obtained from a third party supplier and the American Type culture collection (BAA-471). *S. coelicolor* A3(2) stocks were grown in Yeast-Extract Malt Extract broth (YEME) at 28° C. in 125 mL baffled flasks to an Optical Density at 600 nm ($OD_{600}$) of ~2.0. 20% glycerol was added to the cells in a 1:1 volume ratio and the cells were chilled on ice for 1 hour and placed at −80° C. still in the ice container. After 24 hours the cells were taken out of the ice container and at −80° C. *Streptomyces coelicolor* was grown in *Streptomyces* Minimal Medium (SMM) broth for functional characterization studies. SMM was prepared as previously reported (A17) with the following modifications; L-asparagine was replaced with ammonium sulfate (1 g $L^{-1}$), agar was eliminated and either [56 mM] sodium citrate (SMMC) or [56 mM] glucose (SMMG) was added as the sole carbon source. 50 ml of SMMC or SMMG broths were inoculated with 1 ml of *S. coelicolor* A3(2) stock solutions and grown for 48-72 hrs at 28° C. and 300 rpm shaking in 125 mL baffled flasks.

Cloning was conducted in *E. coli* DH5α cells purchased from Invitrogen (Carlsbad, Calif., USA). *E. coli* JW4251-2 ΔfecA758 cells were obtained from the Molecular Cellular and Developmental Biology Department at Yale University (New Haven, Conn., USA). *E. coli* AA93 Δfec cells were obtained from the Institute of Microbiology II at University of Tuebingen (Tuebingen, Germany). Strains were grown at 37° C. and 250 rpm in Luria-Bertani (LB) broth. AA93 Δfec cells harboring the pET-27b(+)-Sccit plasmid were grown in the presence of [35 μg/ml] kanamycin. JW4251-2 ΔfecA758 cells harboring pET-25b(+)-Sccit plasmid were grown in the presence of [50 μg/ml] ampicillin.

Example 3

Buffers, Broth Ingredients, and DNA Isolation Kits

Buffer and broth ingredients were purchased from Sigma-Aldrich, Becton Dickerson and Company, or Merck and were of biological grade. $^{14}$C-sodium citrate was purchased from Sigma (St. Louis, Mich.). Metal salts were purchased from Sigma-Aldrich and were 99% purity or higher. DNA was isolated using the Promega Wizard Plus SV Miniprep kit. Buffer and broths were made using water that was distilled and deionized to 18.6 MΩ using a Barnstead Diamond ultra-purification system. Chelex was added to all buffers at [15 g/L] and the suspension resulting was stirred overnight. The chelex was then removed by vacuum filtration. This was to ensure removal of metal ion impurities in the buffers. All cells were incubated in a Max$^Q$ 5000 with a digital temperature display. Antibiotics came from EMD or Sigma-Aldrich. The pET-27b(+) and pET-25b(+) expression vectors were purchased from Novagen. All primers were ordered from Integrated DNA Technologies (Coralville, Iowa, USA). Cells were centrifuged with a Sorvall Legend RT tabletop centrifuge at 4000 rpm for 10 minutes at 25° C. Cloning was performed with a TECHNE TC-312 thermocycler. All restrictive enzymes were purchased or provided pro gratis from Promega (Madison, Wis.). Scintillation fluid was PerkinElmer Ultima Gold. Scintillation vials were purchased from Laboratory Product Sales and VWR. All radiation was detected by a PerkinElmer Liquid Scintillation Analyzer Tri-Carbon 2900 TR. Culture density was determined by optical density (OD) measurement at 600 nm ($OD_{600}$) using a Cary 50 Bio UV-visible spectrophotometer in a 1 ml Quartz cuvette.

Example 4

Cloning of Putative Open-Reading Frame for Sccit

The *S. coelicolor* A3(2) cosmid St10A9 containing the open-reading frame (orf) encoding for Sccit was obtained from a third party supplier. The orf was cloned by PCR using Deep Vent polymerase and the following primers:

```
Forward-primer
                                            (SEQ ID NO: 3)
5'-CAGCCATGGCACTGACCATCCTCGGCCTTCG-3'

Reverse-Primer
                                            (SEQ ID NO: 4)
5'-GATGGATCCTCAGATGATGCCGAAC-3'.
```

PCR conditions were as follows: 34 cycles of 95° C. denaturing, 63.0° C. for primer annealing, and 74.0° C. for polymerase chain reaction.

The forward primer introduced a NcoI restrictive site adjacent to the ATG start codon of Sccit. The reverse primer introduced a BamHI site immediately downstream of the stop codon. The PCR product was digested with NcoI and BamHI and ligated (T4 ligase, 16° C., 1 hour) into the pET-27b(+) and pET-25b(+) plasmids that had been previously digested with NcoI, BamHI and calf intestinal phosphatase. The resulting plasmids, designated pET-27b(+)-Sccit and pET-25b(+)-Sccit codes for Sccit fused to the pelB leader sequence at the N-terminus. The correct insertion was confirmed by sequencing performed at the SUNY Upstate Medical University's DNA Core Facility, Syracuse, N.Y., USA. The pET-27b(+)-Sccit plasmid was chemically transformed (30 minutes at 4° C., 45 seconds at 42° C., 2 minutes on ice, recovery for 1 hours in SOC broth at 37° C.) into AA93 zifec cells for expression and functional characterization. The pET-25b(+)-Sccit plasmid was chemically transformed (30 minutes at 4° C., 45 seconds at 42° C., 2 minutes on ice, recovery for 1 hours in SOC broth at 37° C.) into *E. coli* JW4251-2 ΔfecA cells for expression and functional characterization.

Example 5

Metal Speciation

Speciation for all transport assays was calculated using the Visual MINTEQ 2.51 program designed by the Environmental protection agency (A12). MINTEQ values were calculated at a pH of 6.5 and a temperature 30° C. or 37.0° C. as indicated and were calculated to be appropriate to the bacterium.

Table 1 (below) shows the percentage (%) metal-citrate speciation at pH 6.5 and 30° C. (for *S. coelicolor* experiments) calculated using the MINTEQ Program (A12). Excess of metal relative to citrate is calculated to optimize metal-citrate complex formation under set experimental conditions.

TABLE 1

| M ion | Metal conc. [mM] | Citrate conc. [µM] | % Metal-citrate |
|---|---|---|---|
| $Ba^{2+}$ | 10 | 4.4 | 94.244 |
| $Ca^{2+}$ | 10 | 4.4 | 98.261 |
| $Co^{2+}$ | 1 | 4.4 | 99.625 |
| $Fe^{3+}$ | 0.075 | 4.4 | 94.730 |
| $Mg^{2+}$ | 1 | 4.4 | 96.191 |
| $Ni^{2+}$ | 1 | 4.4 | 99.647 |
| $Pb^{2+}$ | 1 | 4.4 | 98.652 |

Table 2 (below) shows the percentage (%) metal-citrate speciation at pH 6.5 and 37° C. (for *E. coli* experiments) calculated using the MINTEQ Program (A12). Excess of metal relative to citrate is calculated to optimize metal-citrate complex formation under set experimental conditions.

TABLE 2

| M ion | Metal conc. [mM] | Citrate conc. [µM] | % Metal-citrate |
|---|---|---|---|
| $Ba^{2+}$ | 10 | 4.4 | 94.103 |
| $Ca^{2+}$ | 10 | 4.4 | 98.110 |
| $Co^{2+}$ | 1 | 4.4 | 99.262 |
| $Fe^{3+}$ | 0.075 | 4.4 | 94.787 |
| $Mg^{2+}$ | 1 | 4.4 | 96.380 |
| $Ni^{2+}$ | 1 | 4.4 | 99.656 |
| $Pb^{2+}$ | 1 | 4.4 | 98.619 |

Example 6

1,5-[$^{14}$C]-Citrate Transport Assay in Whole Cells

Transport in *Streptomyces coelicolor* A3(2)

*S. coelicolor* A3(2) cells were grown from stocks for 48-72 hours at 28° C. and 300 rpm. Cells were collected via centrifugation and washed twice with 50 mM chelexed piperazine-N,N'-bis(2-ethanesulfonic acid) (PIPES) buffer, pH 6.5. Cells were resuspended to an OD of 0.2 after the second wash. 100 µl of cells were added to 2.2 ml microcentrifuge tubes. 5 µl of metal as the chloride salt was then added from the following stock solution concentrations (220 mM $CaCl_2$ or $BaCl_2$, 22 mM $MgCl_2$, $NiCl_2$, 22 mM $CoCl_2$, $PbCl_2$, $MnCl_2$ and 1.65 mM $FeCl_3$). Different molar amounts of metals were used to maximize metal-citrate complex formation as per MINTEQ calculations (A12) and successfully used in a previous literature report (A19). Cells were then incubated at 30° C. for 8 minutes with shaking. At 8 minutes, 5 µl of 96.8 µM 1,5-[$^{14}$C]-citrate was added to each sample to provide a final concentration of 4.4 µM. Uptake was stopped by addition of 2 mL of 0.1 M LiCl. This was followed by immediate filtration through cellulose nitrate filters (0.45 µM, 2.1 cm diameter). The filters were washed with 2×2 mL of 0.1 M LiCl solution and radioactivity was recorded using a liquid scintillation counter. In every experimental run, background radioactivity was gauged by adding 2 mls of LiCl prior to addition of the radiolabelled citrate. As before, cells were then immediately filtered, washed with 2×2 mL of 0.1 M LiCl and radioactivity monitored. This served as the background and was subtracted from final data. Experiments were performed using at least three independent cultures and each time point was collected in triplicate per run. 4×100 µl of cells from each run were filtered directly through pre-weighed cellulose nitrate filter paper and dried to determine average cell sample weight. Transport assays were also 'stopped' using 10 mM HEPES-glucose buffer instead of 0.1 M LiCl to check for the occurrence of 'leaking', which has been postulated to occur with the use of LiCl (A22). No noticeable difference was observed across multiple cultures tested in either *S. coelicolor* (or *E. coli* as described below).

It is important to note that pre-incubating the 'free' metal prior to addition of $^{14}$[C]-citrate or synthesizing the complex and then adding it to the cells made no difference to experimental results consistent with the work reported by Lolkema et al. (A19), except in the case of $Fe^{3+}$. Transport assays with $Fe^{3+}$ were performed at 25.0° C. with the metal precomplexed to [$^{14}$C]-citrate to prevent $Fe^{3+}$ precipitation in the aqueous buffer. The temperature and pH change were accounted for in MINTEQ calculations. All experiments using precomplexed mixtures were filtered using a 0.45 µm syringe filter (Fisher Scientific) prior to addition to cells.

Example 7

1,5-[$^{14}$C]-Citrate Transport Assay in Whole Cells: Transport in *E. coli*

*E. coli* AA93 and JW4251-2 cultures were grown in LB as described above. Protein expression for transport assays was induced at 30.0° C. with 0.5 mM Isopropyl β-D-thiogalactopyranoside (IPTG) at an $OD_{600}$ of 1.0 for 1 hour. Subsequent flux assays followed the protocol described above for *S. coelicolor* and previous literature protocol (A19) with the following adaptations: cells were resuspended with 10 mL of PIPES buffer at 6.5 for all metals, and the transport assay was conducted at 37.0° C. except for iron (25° C.). Non-induced controls were included in all runs. Concentration of metal ion and citrate were chosen to maximize the formation of the desired metal-citrate complex (see Table 2). Experiments were performed using at least three independent cultures and each time point was collected in triplicate per run. Incubation of the metal ion (except for $Fe^{3+}$ as described above) and pre-complexation of the metal with [$^{14}$C]-citrate prior to cell addition yielded similar results. Experiments were also conducted, specifically for $Fe^{3+}$-citrate uptake, involving reducing the IPTG induction temperature in *E. coli* down to 4° C. (see FIG. 5). This was to observe actual uptake of the iron complex.

Example 8

Results

Functional Characterization and Metal Ion Specificity of the Metal-Citrate Complex Transporter from *Streptomyces coelicolor*

While the Sccit was designated a putative metal-citrate transporter, it showed only limited amino acid sequence homology to any functionally characterized CitMHS member to date (35% identity with *E. faecalis,* 39% with *S. mutans,* 42% with CitH of *B. subtilis* and 45% with CitM of *B. subtilis*).

Figure 2:
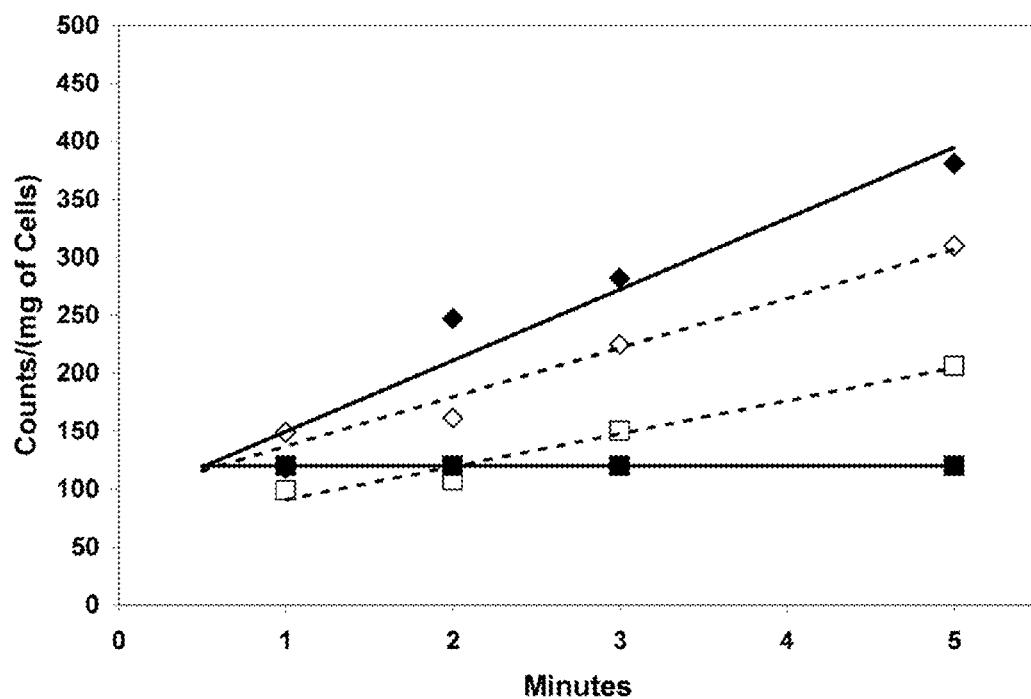
FIG. 2 is a graph showing the effect of addition on increasing concentrations of the chelating agent EGTA on [10 mM] $Ca^{2+}$ uptake. 0.1 mM EGTA (υ), 1.0 mM EGTA (◇), 10.0 mM EGTA (□). At concentrations greater than 10 mM no uptake above 'free' citrate is observed (v).

In *S. coelicolor* grown in broth containing citrate as the sole carbon source no uptake of free citrate was observed. Rather uptake was dependent on the presence of metal ions such as $Fe^{3+}$ and to a lesser extent, $Mn^{2+}$, $Ca^{2+}$, $Ba^{2+}$ or $Pb^{2+}$ (FIG. 1). Concentrations of metal ions were used to maximize the formation of the metal-citrate complex in the assay conditions (see Table 1). When metals such as $Mg^{2+}$ $Ni^{2+}$ or $Co^{2+}$ were added to the reaction mixture uptake of citrate was no greater than the rate of uptake without metal ions. In the presence of the different concentrations of the calcium chelator ethylene glycol tetraacetic acid (EGTA) uptake of citrate in the presence of [10 mM] $Ca^{2+}$ decreased to zero at concentrations of EGTA over 1 mM (FIG. 2). This, combined with no metal-free citrate uptake noted, supports the idea that free citrate is not transported but rather that the presence of select metal ions is necessary for uptake.

Figure 3:
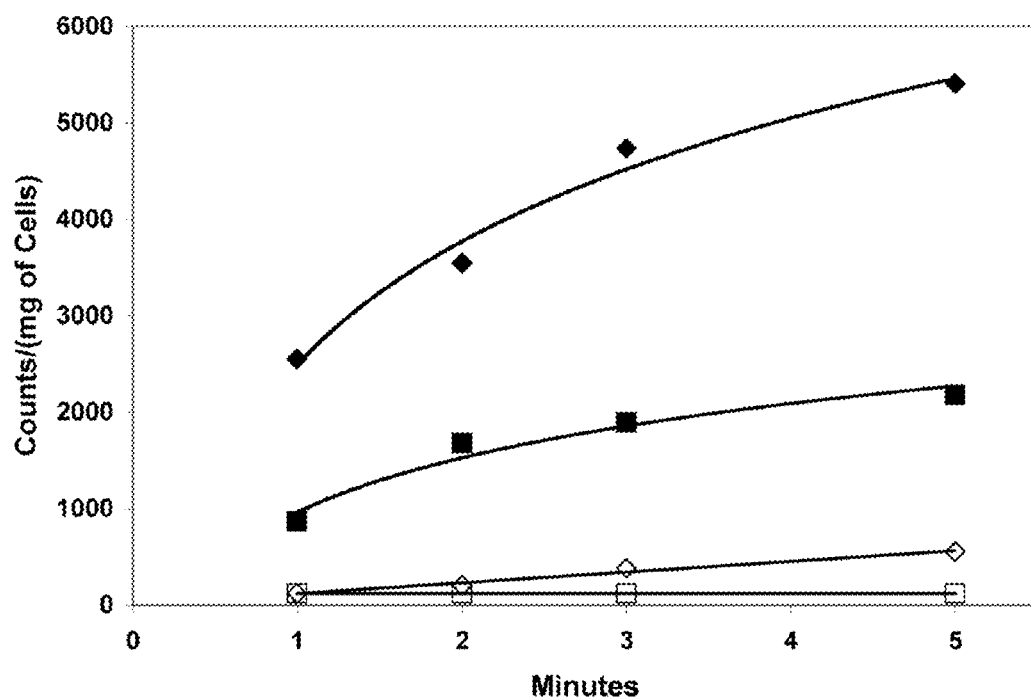
FIG. 3 is a graph showing $Fe^{3+}$-citrate uptake in *S. coelicolor* grown in SMM broth containing glucose as the sole carbon source. (υ) Grown with [36 μM] $Fe^{3+}$ in growth broth, (◇) no iron added to growth broth. (v) 'free' citrate uptake in cells grown in SMMG with [36 μM] $Fe^{3+}$ added to growth broth, and (□) 'free' citrate uptake in SMMG with no added $Fe^{3+}$ to growth broth.
Figure 4A:
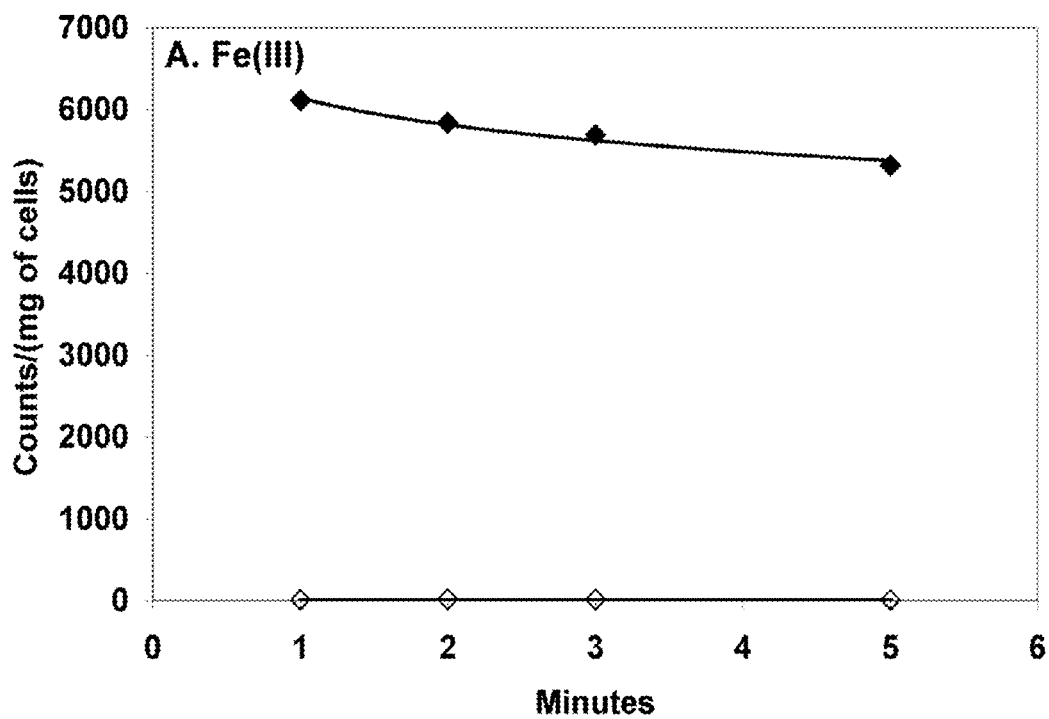
FIGS. 4A-4H are graphs showing the effect of Sccit expression in *E. coli* on the uptake of 1,5-[$^{14}$C]-citrate in the presence (υ), and absence (v), of different metal ions. The graphs represent results from strain JW4251-2 and are characteristic of data collected from both JW4251-2 and AA93 *E. coli*. Note the greater y-axis for FIG. 4A over FIGS. 4B-4H. Non-induced controls are shown as (◇) except where obscured by free citrate controls. The uptake was measured in 50 mM Chelex washed PIPES buffer (pH 6.5) with 75 μM concentration of $Fe^{3+}$ (FIG. 4A), 10 mM concentration of $Ca^{2+}$ (FIG. 4B), $Pb^{2+}$ (FIG. 4C) $Ba^{2+}$ (FIG. 4E), and 1 mM concentrations of $Mn^{2+}$ (FIG. 4D), $Co^{2+}$ (FIG. 4F), $Mg^{2+}$ (FIG. 4G), and $Ni^{2+}$ (FIG. 4H).
Figure 4B:
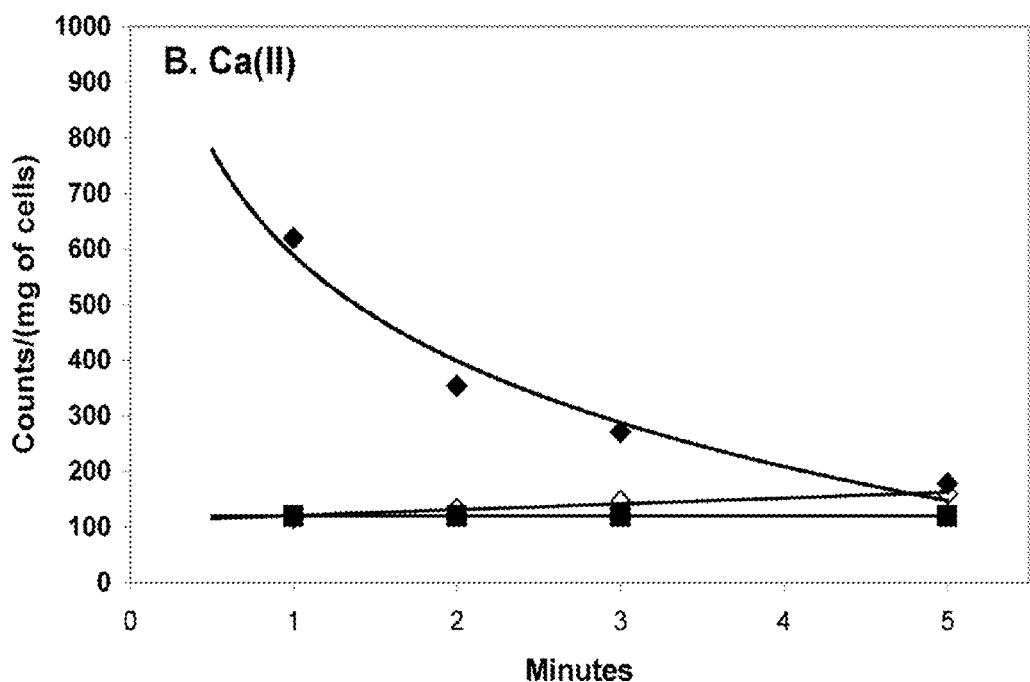
Figure 4C:
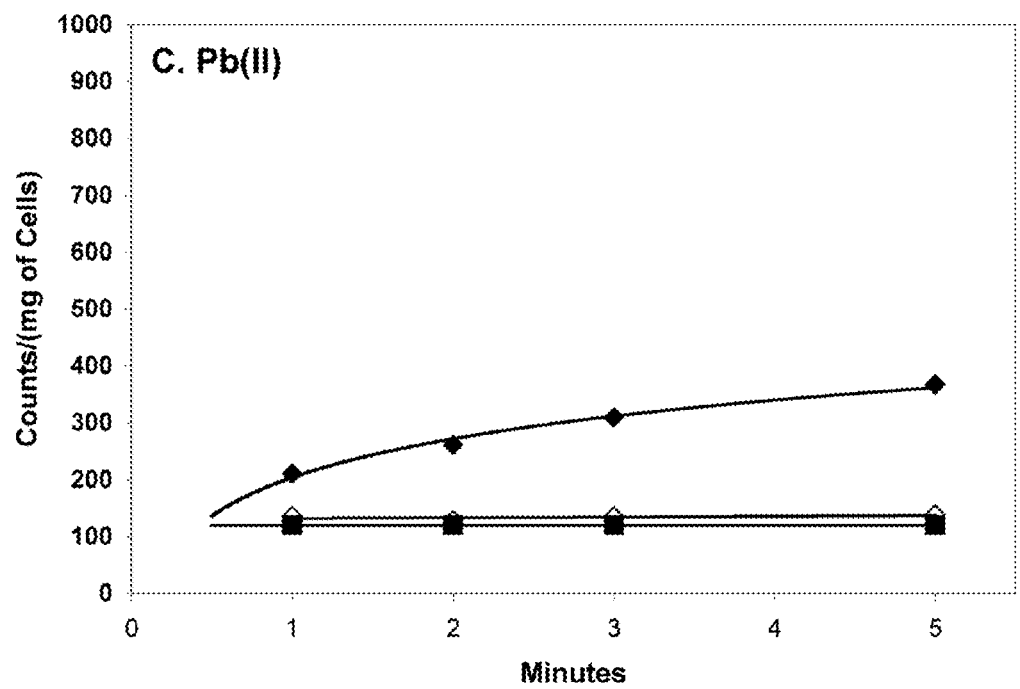
Figure 4D:
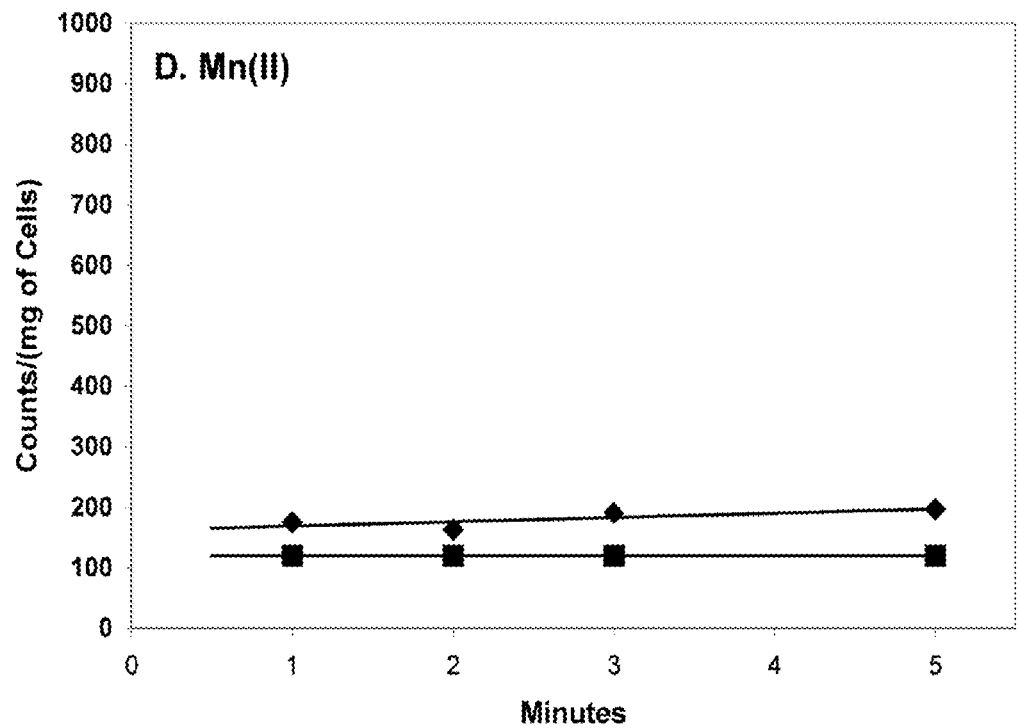
Figure 4E:
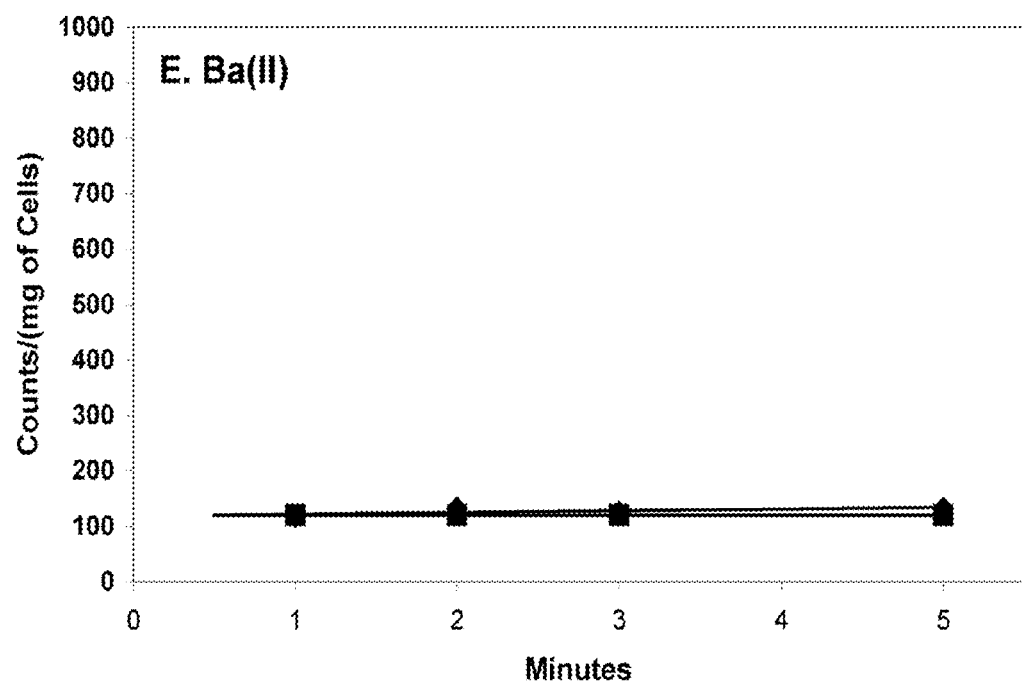
Figure 4F:
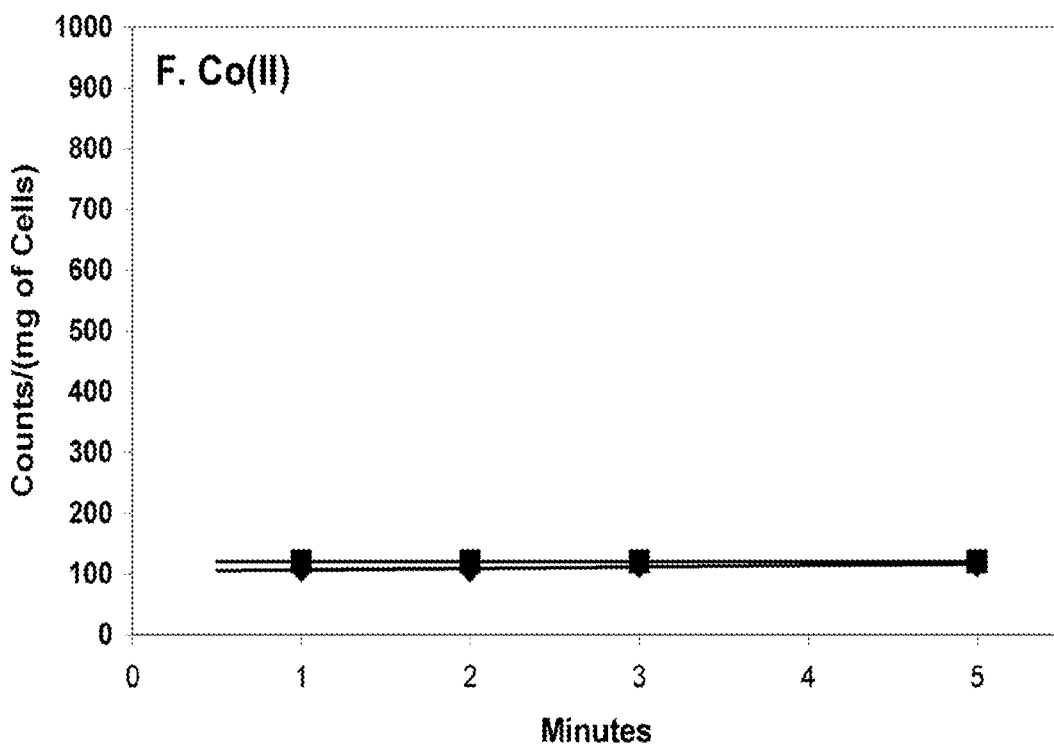
Figure 4G:
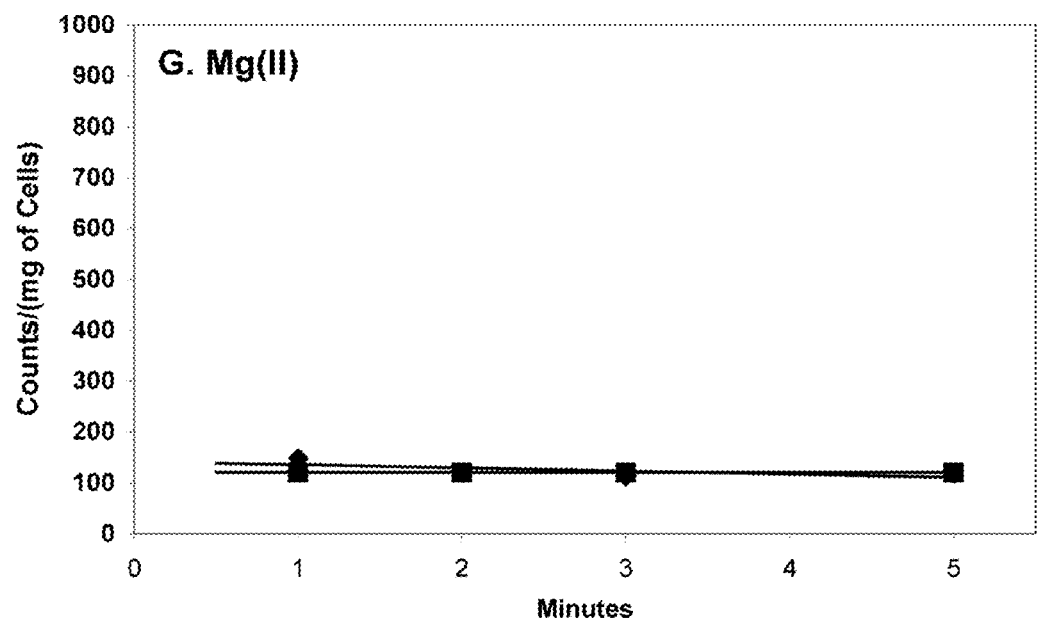
Figure 4H:
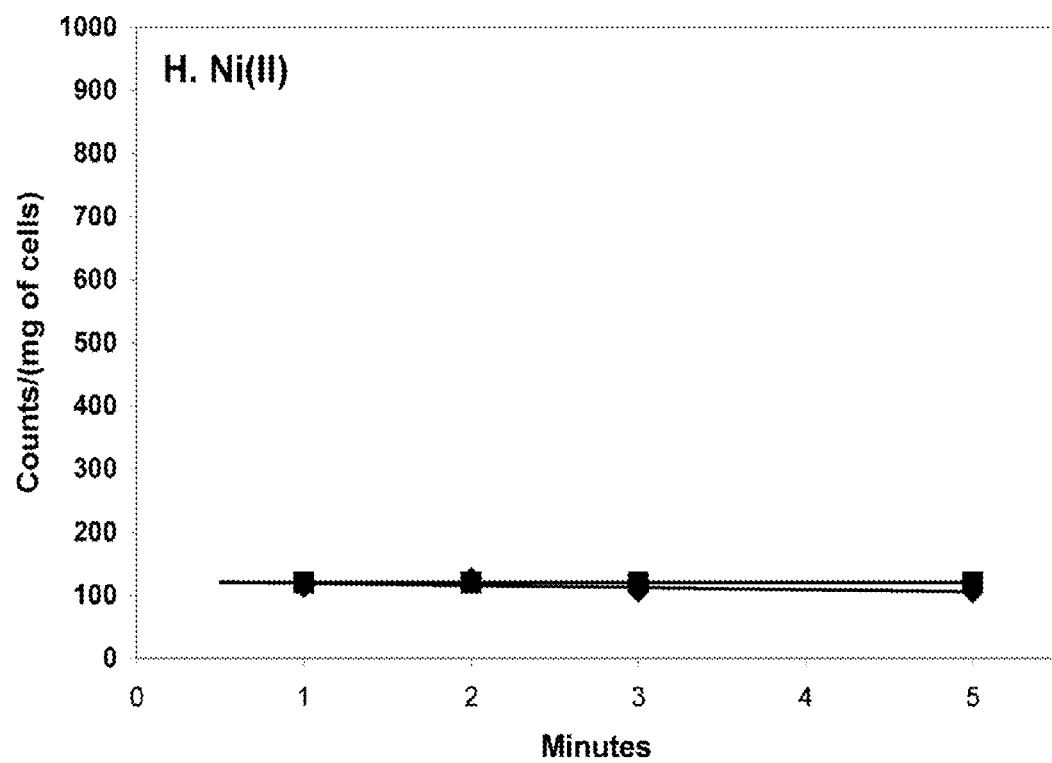

No uptake of any 'free' citrate or metal-citrate species ($Mg^{2+}$, $Co^{2+}$, $Ni^{2+}$, $Ba^{2+}$, $Ca^{2+}$, $Pb^{2+}$) above background was observed when more readily metabolized carbon sources such as glucose were used in place of, or in combination with, citrate indicating expression does not occur in the presence of glucose. The exception to this was with $Fe^{3+}$. A significant uptake above 'free' citrate uptake was observed for iron when S. coelicolor was grown in SMMG supplemented with [36 μM] $FeCl_3.6H_2O$ (see FIG. 3). This implies that the system may be used as an alternate energy source but also an uptake system for iron. Transcriptional control then may be through down regulation in the presence of glucose or up-regulation in the presence of both iron and citrate.

In addition, growth of S. coelicolor was arrested in CHELEX-washed, metal-free SMMC broth. This arrest could be prevented by addition of $Fe^{3+}$ (or $Ca^{2+}$) but not $Mg^{2+}$ or $Ni^{2+}$ to SMMC.

To further investigate the role of the Sccit gene, a number of expression systems were constructed for attempted expression in E. coli (known to be devoid of a 'free' citrate uptake protein under aerobic conditions) (A9). Expression of Sccit in E. coli proved highly toxic in systems tested prior to the use of plasmids utilizing the pelB leader sequence (pET-27b(+) and pET-25b(+)). Cells containing either pET-27b(+)-Sccit (E. coli AA93 Δfec) or pET-25b(+)-Sccit (E. coli JW4251-2 ΔfecA) were successfully induced with 0.5 mM IPTG for 1 hour in LB broth in late log phase with uptake of 1,5-[$^{14}$C]-citrate observed with $Fe^{3+}$, $Ca^{2+}$ and $Pb^{2+}$ metal ions (see FIG. 4). The presence of $Mg^{2+}$, $Ni^{2+}$, or $Co^{2+}$ as cofactors did not result in citrate uptake in E. coli. Uncomplexed citrate was not transported. These results are consistent with uptake in S. coelicolor. No transport was observed when Sccit was not induced by IPTG. It should be noted that E. coli has a primary transport system specifically for $Fe^{3+}$-citrate transport. This system actively binds and transports $Fe^{3+}$-citrate in E. coli and is ATP dependent (A6). As a result transport assays for $Fe^{3+}$ needed to be conducted in E. coli without a functioning fec system. The two strains used in transport assays here had either the cell surface fecA (JW4251-2) removed or the entire fecABCDE operon (AA93) knocked-out. In either case results were the same and indicated $Fe^{3+}$ is a cofactor for citrate transport through the secondary transporter of the CitMHS family.

In the case of $Ca^{2+}$ and $Fe^{3+}$-citrate uptake there is evidence of rapid uptake and metabolization of the transported complex, but the metabolic rates for each complex are notably different. Metabolic differences can be attributed to stability constants and the reduction of iron to the 2+ oxidation state for release. $Ca^{2+}$-citrate has a stability constant of $10^{3.5}$, which allows for intracellular decomplexation to rapidly occur in E. coli. $Fe^{3+}$-citrate has a stability constant of $10^{11.85}$ preventing decomplexation from readily occurring. Instead, E. coli uses systems such as flavins to reduce $Fe^{3+}$ to $Fe^{2+}$-citrate, which has a stability constant of $10^{3.2}$, significantly lower than for $Fe^{3+}$ and similar to that of the calcium complex (A29) (A30). Initial rapid metabolism of $Fe^{3+}$-citrate and subsequent metabolic decrease can be seen in FIG. 4A. The change in metabolic rates may be accredited to the change in concentration of reduced flavin. Reduced flavin formation occurs enzymatically by NAD(P)H:Flavin oxidoreductase in E. coli, which converts flavin into reduced flavin at a $k_{cat}=63\pm2$ $s^{-1}$. Due to the low $k_{cat}$, the rate of reduced flavin formation is below the rate of reduced flavin usage accounting for the change in metabolic rates. A reduction of induction temperature to 4° C. and collection of time points prior to 1 minute 'catches' the E. coli cultures in a period where transportation of $Fe^{3+}$-citrate exceeds metabolic activity yielding a positive initial slope, which solidifies the notion that Sccit is responsible for metal-citrate transportation (see FIG. 5).

Oxidative decarboxylation as part of the tricarboxylic acid cycle would rapidly remove the radioactivity by evolving [$^{14}$C]—$CO_2$ with citrate likely being converted to oxaloacetate and, with subsequent amination, aspartate (A4). Interestingly, while uptake was also observed for $Pb^{2+}$ no reduction in post-uptake concentration indicative of metabolization was observed. Seminal work by Dodge and Francis on the metabolism of metal-citrate complexes can be used to rationalize these results (A8,A9). These researchers found that metal-citrate complexes formed as mononuclear, bidendate species (such as those of $Fe^{3+}$ and $Ca^{2+}$) could be metabolized by Pseudomonas fluorescens but tridendate species (such as those of $Pb^{2+}$) could be transported but were not metabolized. The key they proposed was the presence of an uncomplexed citrate hydroxyl group that may be critical for recognition/binding with aconitase and so subsequent incorporation into the TCA cycle (A9).

Example 9

Discussion

Functional Characterization and Metal Ion Specificity of the Metal-Citrate Complex Transporter from Streptomyces coelicolor In regard to the experimental data and results discussed in Examples 1-8, it is believed that this is only the second example of a gram-positive citrate transporter that preferentially uses ferric ions as a vital cofacter for transport. It is the first such member of the CitMHS to be successfully functionally characterized outside the native organism. It is also believed to be the first to show preferential metabolism of the transported $Fe^{3+}$-citrate species (over $Pb^{2+}$-citrate for example) when expressed heterologously. The Fe-citrate species was also the only species transported above free citrate background when S. coelicolor was grown in SMM containing glucose and iron. The absence of iron from the broth in the same experiment greatly reduced subsequent $Fe^{3+}$-citrate uptake. This suggests S. coelicolor is using this system to acquire iron. While $Fe^{3+}$ was the dominant vital cofactor for transport, other metal ions with ionic radii of ~80 pm and greater ($Mn^{2+}$, $Ca^{2+}$, $Pb^{2+}$ and $Ba^{2+}$) were also transported. Assuming a high-spin, octahedral complex forms for $Fe^{3+}$-citrate (A13) this means an ionic radius of ~79 pm for iron. With the metal ions $Mg^{2+}$, $Ni^{2+}$ and $Co^{2+}$ not transported and having radii less than 72 pm, it appears then that there is an ionic radii role in determining transporter specificity (see Table 3).

Table 3 (below) shows the ionic radii for each metal ion investigated. Metals over 79 pm were transported by Sccit.

TABLE 3

| Metal Ion | Ionic Radius (pm) |
|---|---|
| $Mg^{2+}$ | 66 |
| $Ni^{2+}$ | 69 |
| $Co^{2+}$ | 72 |
| $Fe^{3+}$ | 79 |
| $Mn^{2+}$ | 80 |
| $Ca^{2+}$ | 99 |
| $Pb^{2+}$ | 119 |
| $Ba^{2+}$ | 134 |

Clearly specificity does not correlate with the formation of bi- or tri-dentate complex formation since both the tridendate $Pb^{2+}$ and bidendate $Ca^{2+}$ and $Fe^{3+}$ are transported. This is in agreement with the work of Lolkema (A27) and Francis (A8, A9). Lolkema has instead described a "size criterion" that is the result of the physical size of the protein binding site as playing a major role in determining specificity (A4). The difference in $Mn^{2+}$ and $Fe^{3+}$ transport however, despite the similar ionic radii between the two metal ions, suggests that complex speciation and/or coordination geometry may still play a part with the presence of an $Fe^{3+}$ bound hydroxyl group in the [Fe(III)(OH)-cit]⁻ complex (but not found in the $Mn^{2+}$-cit complex for example) playing a role (e.g. H-bond donor in the binding pocket). The two most common citrate-to-metal binding motifs are a linear citrate backbone or one with the citrate backbone 'bent'. The manganese is found with the linear arrangement (A23). Iron-citrate structures described by Salifoglou et at describe the citrate in the 'bent' arrangement for $Fe^{3+}$ (A24). This may also explain the difference between $Fe^{3+}$ uptake over $Mn^{2+}$. Another potential effect may arise from complex charge with the manganese complex monovalent and the $[Fe(III)(OH)_2$-cit] complex both a mono- and a di-valent species. The presence of both of a monovalent (68.2%) and divalent (31.8%) Fe-citrate species was calculated using MINTEQA2 (A15). Interaction with the additional negative charge of the $[Fe(III)(OH)_2$-cit]$^{2-}$ complex may play some role in greater iron transport over manganese and indeed over other metals forming monovalent complexes ($Ca^{2+}$, $Pb^{2+}$, $Ba^{2+}$, $Mg^{2+}$, $Co^{2+}$, $Ni^{2+}$) in general. Interestingly, it is the divalent species that was metabolized in studies in *P. fluorescens* conducted by Francis (A15).

*S. coelicolor* transports $Fe^{3+}$-citrate when grown in SMMG broth containing $Fe^{3+}$, but does not transport $Fe^{3+}$-citrate when $Fe^{3+}$ is omitted from the growth media. This suggests that the Sccit protein system may be used primarily to access iron and not to access citrate. Given *S. coelicolor* is a dominant bacterium in the soil environment it must be capable of surviving in such an environment. The ability to access trace vital elements such as $Fe^{3+}$ is critical for survival and would give *S. coelicolor* a competitive advantage in such a competitive environment. Cvitkovitch postulated this with his work on *S. mutans*, a major cause of dental caries (A20). He suggested that *S. mutans* was using the Smcit transporter to gain access to $Fe^{3+}$ in humans. Lolkema attempted to find a similar iron uptake result in *E. faecalis*, which he noted had a 75% sequence homology to the Smcit $Fe^{3+}$-citrate transporter of *S. mutans* (A4, A26). He found instead the system to be a predominantly $Ca^{2+}$-citrate with no iron-uptake. Clearly these systems are being controlled by a yet unknown subtle mechanism that controls for such exquisite metal-citrate selectivity (A10). The importance of this work in *S. coelicolor* lies in the importance of iron limitation in blocking infection by pathogenic bacteria. For example, a single injection of iron was shown to decrease the lethal dose of *Pseudomonas aeruginosa* (in a murine infection model) from more than $10^4$ organisms to fewer than 10 (A7,A16). While not a pathogenic bacteria, *S. coelicolor* is a member of the Actinomycete family, which also includes *Mycobacterium tuberculosis* and *Bacillus anthracis*. The ability to access iron from iron citrate found in blood plasma would give *M. tuberculosis* a possible route to overcome iron-based bacteriostasis (A5,A27). High iron concentrations are also necessary for biofilm formation, which implies access to higher levels of iron would promote pathogenesis in a biofilm forming bacterial genus such as *Mycobacteria* (A2, A26). Chemical speciation models actually indicate that, amongst the naturally occurring low molecular mass ligands, a dominant $Fe^{3+}$-citrate species is formed at concentrations as low as 1 mM in serum (A18). Sequence homology study of the Sccit amino acid sequence against the *M. tuberculosis* genome found a sequence with 57% homology based on nucleotide sequence. Recent work was begun on this gene to investigate if it is indeed a member of the CitMHS family and to compare it to Sccit and Smcit. Mutagenesis studies were also begun on Sccit to attempt to elucidate the mechanism behind this extraordinary uptake process.

Example 10

The CitMHS Superfamily of Integral Membrane Proteins

Most bacterial citrate transporters carry free citrate coupled to protons or sodium and are inhibited by the addition of di- or tri-valent cations since they do not recognize the metal-citrate complex formed.[5] Some unusual transporters, however, have evolved in strains of species such as *Bacillus, Citrobacter, Neisseria, Klebsiella* and *Streptomyces*, that specifically recognize citrate in complex with divalent metal ions.[6] It is believed that these organisms take up complexed citrate because it is predominantly available as such in their habitat. To date, the only functionally characterized systems for metal-citrate transport in this family are those of *Bacillus subtilis, Streptococcus mutans, Enterococcus faecalis*[4c] and most recently that of *Streptomyces coelicolor*.[54] These members of the CitMHS family transport metal-citrate complexes in symport with one H⁺ per metal-citrate. Lolkema et al. demonstrated that CitM from *B. subtilis* transported citrate in complex with $Mg^{2+}$, $Ni^{2+}$, $Mn^{2+}$, $Co^{2+}$ and $Zn^{2+}$ but not in complex with $Ca^{2+}$, $Ba^{2+}$ and $Sr^{2+}$. CitH, also from *B. subtilis*, transported citrate complexed to $Ca^{2+}$, $Ba^{2+}$ and $Sr^{2+}$ but not $Mg^{2+}$, $Ni^{2+}$, $Mn^{2+}$, $Co^{2+}$ and $Zn^{2+}$.[4a] Clearly the group of metal ions transported by CitM includes the smaller cations, with a Pauling radius of less than ~0.80 Å. The ions transported by CitH of *B. subtilis* have radii larger than 0.98 Å. More recently Cvitkovitch et al. functionally characterized the CitM homolog from *Streptococcus mutans*.[4b] Citrate complexed to $Fe^{3+}$ and $Mn^{2+}$ was transported in this case, however, $Ca^{2+}$, $Mg^{2+}$ and $Ni^{2+}$ were not. Cvitkovitch in fact states that iron is the most efficient cofactor for citrate uptake in *S. mutans*. This suggests the intriguing possibility that, given *S. mutans* is considered a major etiological agent of dental caries and oral cancer, it may be using the system to access essential iron and so play a role in pathogenesis. Given members of the CitMHS family are postulated in bacteria such as *B. anthracis* and *Neiserria* spp., it is important to have a better understand these systems. A fourth system characterized in native membranes is that of the transporter in *E. faecalis*.[4c] High amino acid sequence homology (73%) to the sequence of *S. mutans* led researchers to believe, as with *S. mutans*, it could be an iron transporter. Instead the system was shown to be a CitH (*B. subtilis*) homolog, transporting larger ionic radii metals such as calcium. The transporter of *S. mutans* itself had been predicted to be a transporter for $Mg^{2+}$. This unpredictability clearly demonstrates a limited understanding of these systems. Sequence homology, while a good predictor of the presence of a CitMHS family member, clearly does not yet allow one to predict metal co-factor preference.

Figure 7:
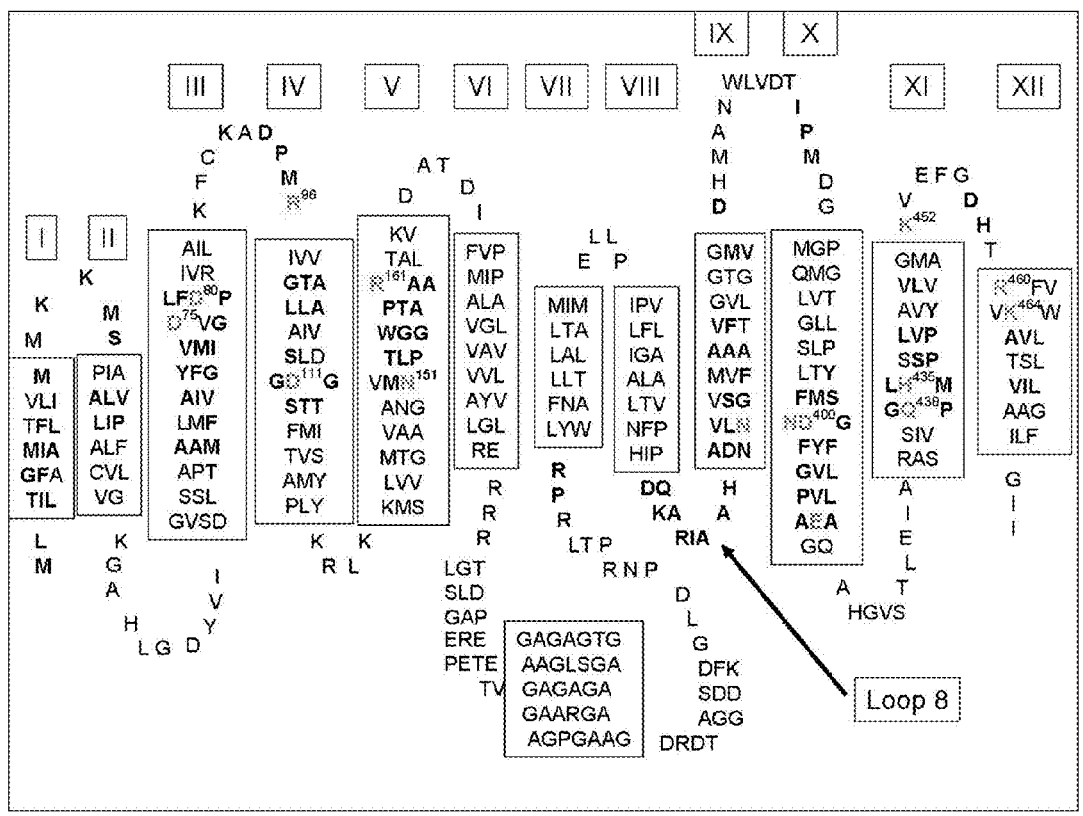
FIG. 7 is a schematic showing a model of the predicted membrane topology of SEQ. ID. NO. 1, where the $Cit_{Sc}$.[28] C-terminal region is predicted to be outside the membrane with the N-terminal region inside. Boxes indicate transmembrane helices. Residues to be mutated initially are marked. Residues in orange and blue will be mutated as described herein.
Figure 8A:
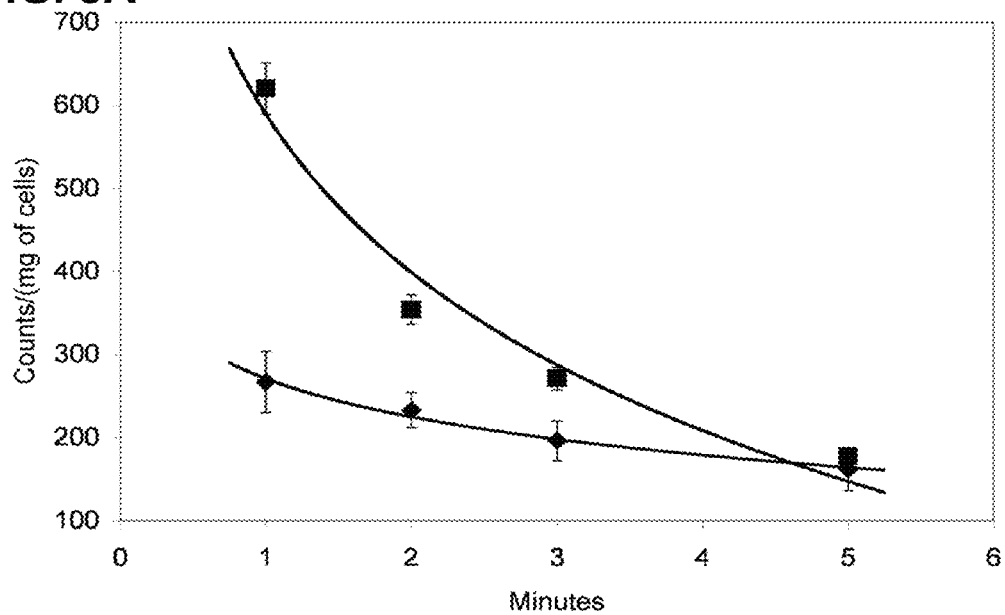
FIGS. 8A-8B are graphs showing the uptake of $Ca^{2+}$-citrate in *E. coli* (JW4251-2) overexpressing the $Cit_{Sc}$-R460C mutant (left, FIG. 8A) and K452C mutant (right, FIG. 8B). Comparison is shown between $Cit_{Sc}$ (■) and each mutant (♦). Results demonstrate the importance of the positive charges provided by K452 and R460.
Figure 8B:
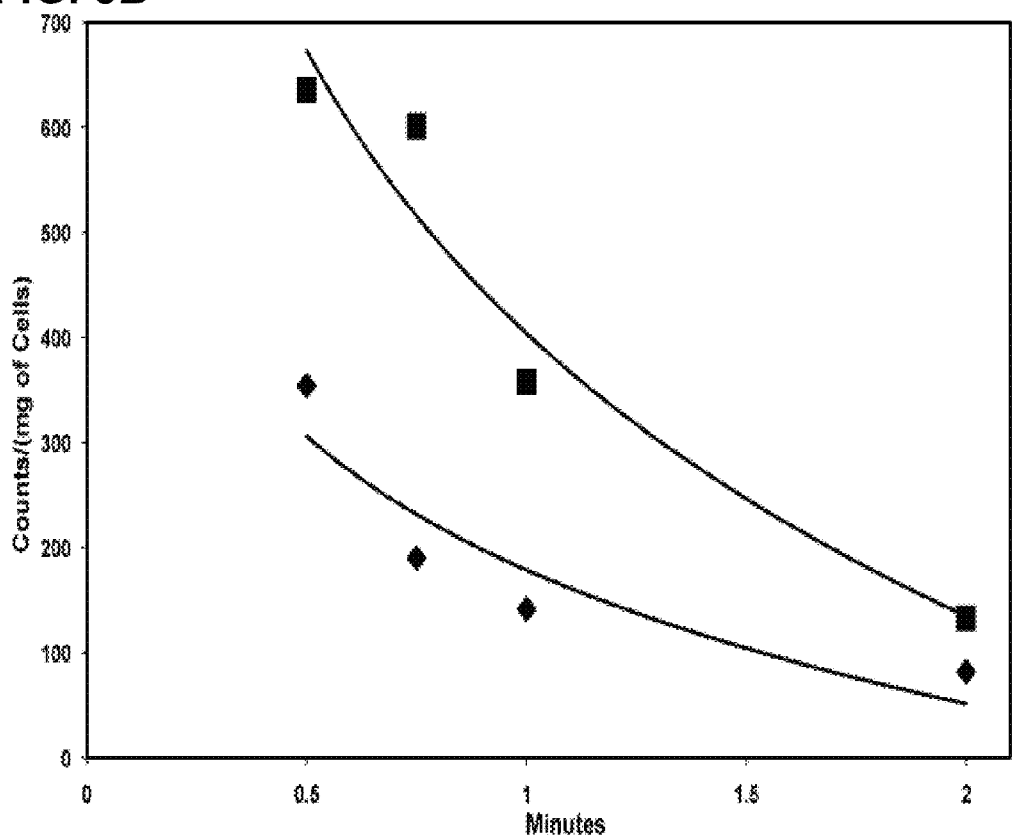

No structure has been published for any member of the CitMHS family nor has a comprehensive over-expression and mutagenesis study been reported at this time. Over-expression and mutagenesis studies have been conducted for uncomplexed 'free' citrate transportors however. Lolkema et al. have shown in citrate transporter proteins such as CitP of *Leuconostoc mesenteroides*[7], that an arginine residue in the C-terminal transmembrane helix (TMH XI) is responsible for high affinity binding of di- and tri-carboxylates (see FIG. 7). This arginine residue (R460 based on numbering for *S. coelicolor* used in FIG. 6) is conserved in other 'free' citrate transporters compared but has been replaced by a conserved lysine residue for metal-citrate transporters except in the case of *S. coelicolor*, which has maintained the arginine (see FIG. 6). Mutation studies conducted on the 'free' citrate transporter CitP, producing a switch from R to K, demonstrated that CitP had lower affinity for its citrate substrate.[7] Another mutant, replacing the R positive charge with neutral cysteine stopped transport indicating that a positive charge is vital. Given R and K both provide a positive charge but the K mutant has lower citrate affinity it appears that it is not simply charge playing a role here. K has less ability to form H-bonds compared to R and the guanidinium group of R had an unusually strong interaction with 'hard' carboxylate groups. If this residue is shown to have similar effects in the CitMHS family, it is tempting to suggest that *S. coelicolor* may have greater affinity for the same metal-citrate complex over a CitMHS member with K at this position (such as CitM from *B. subtilis*). It is also of note that a second arginine residue, this one in the cytoplasmic loop between TMH X and TMH XI, known to be vital for the activity of CimH 'free' citrate transport (mutation to cysteine removes all transport activity) is not conserved for CitMHS transporters of *B. subtilis* (CitM and CitH) or in *S. coelicolor* (residue 449) but is conserved in those from *E. faecalis* and *S. mutans*. The question of solvent exposure of this R residue is, of course, important. It was shown upon mutation of this R residue to C and exposure to membrane permeable and impermeable thiol reagents that in CimH this residue is accessible to the external face of the membrane.[9] The cytoplasmic loop is postulated to traverse the membrane and form a reentrant loop-like structure.[9] This is not unprecedented having been shown in GLP-1 of the central nervous system[10] and in Glt-T of *B. stearothermophilusil* for example.

It is important to note that, in addition to changes in protein sequence, important changes occur to citrate upon metal chelation. Citrate chelates divalent metal ions in the majority of cases through one of its three-carboxylate groups and its 2-hydroxy group. Since transporters for free citrate have been shown to have high specificity for 2-hydroxycarboxylate motifs this may go a long way to explain the loss of binding to complexed citrate of 'free' citrate transporters where the hydroxyl group is involved in binding the metal ion. How the metal-citrate transporters overcome this is unknown but a possibility may be interactions between metal-binding residues such as histidine or aspartic acid for example. Interestingly, *S. coelicolor* and both *B. subtilis* sequences have a His residue next to the conserved loopbound Q residue adjacent to TMH XI. This is an alanine residue in 'free' citrate transporters. No directly analogous H residue is observed in *S. mutans* or *E. faecalis* although proximal D and E residues are present, which have no counterpart in that region of the 'free' citrate transporters. What is clear is that there are important sequence differences between free citrate transporters and metal-citrate transporters. What is also clear is that simply classifying uptake based on the size of the metal's ionic radius is not sufficient. Complex speciation, charge, citrate metal binding sites involved, H-bonding, and protein metal interaction all have important potential roles to play (see Reference 54).

Example 11

Studies on the CitMHS Family of Transport Proteins

To advance the understanding of the CitMHS family of transport proteins, three major objectives are to be pursued, including: (i) conduct metal-citrate uptake flux assays and control experiments in *S. coelicolor* A3(2); (ii) characterize $Cit_{Sc}$ and $Cit_{Sc}$ mutants overexpressed in *E. coli* and/or incorporated in membrane vesicles; and (iii) chemically characterize the *E. coli* overexpressed and purified $Cit_{Sc}$ and investigate the structure of $Cit_{Sc}$.

The experimental design for each objective is based on the hypothesis on the role of $Cit_{Sc}$ and the postulated structure-function relationship. The role of $Cit_{Sc}$ is that of an integral membrane bound energy independent symport protein (i.e. catalyzes electrogenic proton/substrate symport), similar in simple model terms to lac permease (LacY) of *E. coli*[22]. It is believed that the protein's primary function is the transport of iron(III)-citrate, as a mechanism to obtain iron primarily. Focusing on structure-function, it is predicted that the protein contains twelve transmembrane helices and, using the known structures of the $Na^+/H^+$ antiporter,[23] the glycerol-3-phosphate transporter,[24] and the lacY transporter as starting points, a model has been built as to what the protein looks like and how it functions. The model has twelve transmembrane alpha helices with eleven helical loops (five exposed to the cytoplasm and six to the periplasm or extracellular environment). Both the N- and C-terminii are exposed to the cytoplasm. Each helix contains at least fifteen amino acids most of which are hydrophobic (Val, Pro, Leu, Gly, Ala). The loops contain at least four amino acids and usually contain several charged amino acids such as arginine, aspartate, histidine, and glutamate.

When the multiple sequence alignment of the five investigated CitMHS members are compared, one can see six highly conserved regions in the alpha helices (III, IV, V, IX, X, XI) and 1 conserved loop (Loop 8). Looking at the known structures of the glycerol-3-phosphate transporter and lacy in particular, it is noted that up to 8 alpha helices are involved with actual recognition and transport of substrate transport. The remaining helices contribute to structure. Using this information it was hypothesized that the following protein regions are critical for function in $Cit_{Sc}$ (see FIG. 7):

Alpha helix III. The Alpha helix III has a large central conserved area with two aspartic acids at residues 75 and 80. A non conserved arginine but conserved positive charge or hydrogen bond donor is found near the aspartic acids. These aspartic acids play several critical roles: (1) create a salt bridge to attract and move protons, (2) hydrogen bond with one of the arginine terminal amines to localize the positive charge on the other for substrate affinity, (3) hydrogen bond to lysine to increase the electrophilicity of the nitrogen to form hydrogen bonds with the substrate, and (4) hydrogen bond to other amino acids to stabilize the protein. Arginines and lysines are critical for citric acid recognition as seen in the FecA protein of *E. coli*,[25] the chemoreceptor Tcp of *Salmonella enterica*,[26] and the catalytic center of the 2-methylisocitrate lyase from *E. coli*.[27]

Alpha helix IV. The Alpha helix IV remains also highly conserved. Another aspartic acid at D111 and a possible contributing arginine at the helix cap (R96) may be important for citrate acquisition.

Alpha helix V. The Alpha helix V contains a very highly conserved area. Arginine 161 is fully conserved in the five CitMHS members explored to date, as is N151. The arginine is probably critical for citrate recognition while N151 possibly plays a role in hydrogen bonding to the coordinating water molecules as observed in the chemoreceptor Tcp.[26]

Loop 8. Loop 8 is highly conserved. It is likely to be a pH response domain as seen in the $Na^+/H^+$ transporter. As the pH decreases the domain becomes protonated and causes a conformational change that inhibits the symport of the metal-citrate with protons.

Alpha helix X. Alpha helix X has a highly conserved area. N399 is flanked by an aspartic acid. The asparagine might recognize the citrate or a coordinated water molecule. A glutamate is also found near the cytoplasmic cap that could participate in hydrogen bonding.

Alpha helix XI. Alpha helix XI is moderately conserved. There are three major residues of interest on this helix. Histidine 435 may be involved in coordinating to the citrate residue and or forming a salt bridge with one of the aspartic acids, glutamic acid, or arginine found on an adjacent helix. Glutamate 438 is likely to be hydrogen bonding to the citrate or a water molecule. Finally, there is a fully conserved lysine at the extracellular cap that is conserved through all the members. It is likely that this lysine is important for external citrate acquisition.

Alpha Helix XII. Alpha Helix XII is not well conserved but there are two residues that seem important to us. The arginine at 460 is not strictly conserved but is found replaced only by a lysine in other CitMHS members. The arginine, or lysine, then are likely important for citrate acquisition and or recognition. A lysine residue (K464) is fully conserved across all members and likely binds to citrate.

Example 12

Conducting of Metal-Citrate Uptake Flux Assays and Control Experiments in *S. coelicolor* A3(2)

Metal ion specificity will be determined in native *S. coelicolor* A3(2) in the presence of citrate and metal ions as the chloride salts. It will be demonstrated which metal ions promote citrate uptake and, vice versa, if citrate promotes uptake of any metal ion. This would clearly indicate that a complex is the transported species. This uptake will be measured using the rapid-filtration transport assay as described by Lolkema et al.[4a] This involves measuring uptake of radiolabeled substrate, in this case [1,5-$^{14}$C] citrate (114 mCi/mmol). Reactions are controllable and can be stopped by addition of cold LiCl solutions. In the case of metal-citrate uptake, an excess of metal ions will be used to ensure the citrate is driven into the complexed state.[29] All buffers used will pass through 15 g/L chelex resin (Sigma) for 18 hours to remove metal ion impurities prior to use. Metals to be investigated are $Fe^{3+}$, $Mg^{2+}$, $Ni^{2+}$, $Co^{2+}$, $Mn^{2+}$, $Zn^{2+}$, $Ca^{2+}$, $Sr^{2+}$, $Ba^{2+}$, $Hg^{2+}$, $Cd^{2+}$, a chosen for their biological importance and/or established citrate coordination chemistry. For experiments studying the inhibition of citrate transport by other substrates such as isocitrate or cis-aconitate, an excess of inhibitor will be used in the presence of a metal-citrate system that is transported by $Cit_{Sc}$ (e.g. $Ca^{2+}$-citrate). The kinetic parameters, including affinity for the complexes, will be estimated from the initial rates of uptake in cells expressing the $Cit_{Sc}$ protein using the methods described by Pajor et al.[30] The time course of complexed citrate uptake and uptake as a function of citrate concentration will be established in this way (Fit to the Michaelis-Menten or Hill equations using standard non-linear regression protocols).

Example 13

Characterization of $Cit_{Sc}$ and $Cit_{Sc}$ Mutants Overexpressed in *E. coli* and/or Incorporated in Membrane Vesicles The first concern upon starting this objective is whether incorporating $Cit_{Sc}$ into *E. coli* will result in toxicity. Preliminary results, noted later, indicate that when expressed as the pelB fusion tagged system coupled with a His-fusion tag, it is not immediately fatal to the bacteria with growth continuing post-induction. *E. coli* cells with the primary $Fe^{3+}$-citrate transport system removed were used to ensure no 'background' uptake occurred (e.g. Δfec).

The pelB tagged system can be used for gain-of-function transport flux assays in *E. coli* to confirm if $Cit_{Sc}$ (SCO1710-see Examples 1-9) is responsible for the transport of metal-citrate complexes in *S. coelicolor*. The effect of pH and the presence of ionophores (nigericin, trifluoromethoxy-phenyl-hydrazone (FCCP) and valinomycin) will aid in the understanding of the mechanism behind $Cit_{Sc}$. Using right side out membrane vesicles containing the $Cit_{Sc}$ protein, the vesicles will be energized using the potassium ascorbate-phenazine methosulfate (PMS) electron donor system. In the presence of a proton-motive force (PMF) metal-citrate uptake will be measured. Should accumulation of citrate be noted these experiments would establish that $Cit_{Sc}$ is a secondary transporter, utilizing the PMF to drive uptake and not ATP. Proton co-transport (or counter-transport) will also be investigated by modifying the pH, increasing it beyond 7.5 in this case. This will disrupt uptake by dissipating the pH gradient across the membrane and further establish the secondary transport hypothesis. The presence of ionophores will also serve to disrupt the transmembrane pH gradient or membrane potential component of the PMF and so will yield valuable mechanistic insight into transport by $Cit_{Sc}$. Membrane vesicles will be constructed using standard literature procedure but summarized as follows: *E. coli* containing the pET25-b(+)-$Cit_{Sc}$ vector will be induced and grown into the late log phase. Cells will be harvested by centrifugation and membrane fractions will be isolated using the established procedure from Kaback and Stadtman.[31] *E. coli* liposomes will be fused with liposomes containing beef heart cytochrome c oxidase to create a proton gradient as established by Konings et al.[32] Vesicles containing the $Cit_{Sc}$ and cytochrome c oxidase will be made unilamelar by sonication and stored at -80° C. Transport studies will be conducted by energizing the vesicles with 200 μM N,N,N',N'-tetramethyl-p-phenylenediamine (TMPD), 20 mM cytochrome c and 10 mM potassium ascorbate as established by Bandell et al.[33] Additional studies will be conducted to prove the secondary transport by using ionophores (e.g. valinomycin and nigericin) and procedures established by Bandell et al.,[33] which will destroy the chemical gradient by creating pores and equilibrating the proton concentration.

Example 14

Mutagenesis Studies

As discussed earlier certain amino acid residues have drawn interest and others are described here. Those residues of primary concern are highlighted in FIG. 7. Site-directed mutagenesis will be used to produce the mutants noted below. The aim here is to explore how the $Cit_{Sc}$ structure affects function. Residues below were selected based on the hypothesis of what are critical protein regions/residues in $Cit_{Sc}$.

H458A: Histidine is a well-documented, ubiquitous, metal chelator and hydrogen-bond donor and is present in the Cit-MHS family in a region predicted to be central for substrate uptake. Given the residue is conserved as an alanine in free citrate transporters, converting H to A may greatly diminish metal-citrate affinity or uptake if H is indeed vital. If this occurs it would be important to see if the system subsequently displayed changes in affinity for, and uptake of, 'free' citrate.

H458C: Should H458 be shown to be important, establishing whether it interacts with citrate or metal in the metal-citrate complex would be of interest. One route would be through mutation to C. Conducting subsequent thiolation reactions using membrane impermeable thiols (MTSES) with and without citrate present could gauge if citrate 'protects' C from thiolation indicating interaction at that position. This ligand protection of Cys-mutant thiol modification will be performed for all suitable Cys mutants produced.

R460K: Lowering pKa by switching from R to K and assaying for affinity will allow comparison between homologous complex uptake between *S. coelicolor* and *B. subtilis*, for example, which have R and K respectively at these positions. One quest to be answered is whether R provides greater affinity for similar complexes to the *Streptomycete* over *Bacillus*.

D111A: The aspartic acid at the D111 is predicted to participate in the formation of a salt bridge that facilitates the transport of protons across the cellular membrane. By changing this aspartic acid to an alanine one can observe any change in the uptake patterns of $Cit_{Sc}$ that might be due to the disruption of the putative bridge.

D75A & D80A: The aspartic acids at residues 75 and 80 positions are likely to also be participating in salt bridge formation or hydrogen bonding for stabilizing the substrate recognition site. By mutating these aspartic acids to non-hydrogen bond donors such as alanine one should see a decrease in metal-citrate uptake.

R161A: Arginines are critical for citrate recognition as seen with the Tcp chemoreceptor and the FecA protein. There are few conserved arginines amongst the CitMHS members designated to be within an alpha helix, but the R161 is fully conserved. Mutation of the arginine to an alanine is expected to significantly impact metal-citrate transportation.

N151A & Q438A: Asparagine and Glutamine are known to participate in hydrogen bonding as well as possible salt bridge formation. Asparagine and glutamine can participate salt bridge formation, citrate complexation, and coordination to the water molecules surrounding the metal ion.

H435A: Histidine is known to complex with metal ions. Additionally, histidine can contribute to stability through hydrogen bond formation. Histidine is also important for formation of salt bridges and proton recognition as seen in the LacY protein.[22] If disruption is observed one can change the mutant to positively charged lysine and see if transport is restored.

K452C: The K452 amino acid was predicted to be surface exposed and contribute to citrate acquisition. By building the K452C mutant the positive charge is substituted for a neutral hydrophobic group, therefore less positive charge is available on the protein surface to attract the negatively charged citrate, which is predicted to decrease the uptake of metal-citrate complexes.

R460C: The R460 amino acid was predicted to be surface exposed and contribute to citrate acquisition. By building the R460C mutant the positive charge is substituted for a neutral more hydrophobic group, therefore less positive charge is available on the protein surface to attract the negatively charged citrate, which is predicted to decrease the uptake of metal-citrate complexes.

K464A: The K464 amino acid is predicted to be in the XII alpha helix. Since only one arginine is predicted in all 12 alpha helices and citrate needs multiple positive charged species, K464 is expected to be involved with substrate recognition. By building the K464A mutant, a decrease in transport of metal-citrate is expected to be observed.

It is important to note that there are two other C residues present in $Cit_{Sc}$. Reaction of the native protein with impermeable (MTSES) and permeable (MTSEA) thiols, affinity assays, and activity will be conducted prior to mutant construction to see if these residues affect protein function as control. If this is the case, suitable mutation at these positions will also be pursued. In addition, mutations will be made to random sites, not believed critical to function, of the protein to gauge whether structural change might impact transport activity (e.g. D109A).

Studies replacing citrate with similar di- and tri-carboxylic acids such as isocitrate, succinate, aconitate and tricarballic acid will also be conducted and should provide information on substrate specificity. All of these acids are capable of binding metal ions and so in the presence of citrate are expected to compete with citrate for metal ion binding with concomitant decrease in metal-ion uptake. In this manner inhibition studies can be performed. These experiments will be conducted for the native protein but also for all mutants designed and expressed in whole cells or incorporated in vesicles as required.

Example 15

Chemical Characterization of the *E. coli* Overexpressed and Purified $Cit_{Se}$ Binding studies will be conducted at different protein, metal and citrate concentrations and between pH 5 and 9 (or acid/base range that protein can tolerate). A rapid method to screen for metal-citrate binding to the protein, which uses a minimum of protein, is ultraviolet-visible spectroscopy and where applicable this will be used. Changes in the spectrum upon binding can indicate particular residues are involved (e.g. a ligand to metal charge transfer band between cysteine and cobalt is known to produce a new peak at ~545 nm compared to the apo-protein).[34] Such changes can display as an increase in extinction coefficient of peaks in the 200-400 nm range. Kinetics studies to determine rate of binding could then be conducted and stability of the holoprotein monitored. Information regarding metal coordination and geometry can also be isolated using this approach. Inductively coupled Plasma-mass spectrometry or Atomic absorption can also be used to determine metal-citrate binding, including how many metals are bound (predicted to be one metal-complex per protein). Characterization will also utilize any paramagnetic metal ions such as cobalt (II) that are transported as a citrate complex, which will allow study by electron paramagnetic resonance (EPR). Such a technique could provide valuable information such as metal spin state, oxidation state and coordination number and has been extensively used in the study of metallo-enzymes. The continuous wave EPR spectra of the metal-citrate complex, free of protein, will also be obtained to provide information on the impact protein bind-

Example 16

Structural Investigation of Cit$_{Sc}$

Having established access to 0.2 mg per liter of fusion His tagged-Cit$_{Sc}$ is a big step to this goal. Work is being done to scale up production to allow for storing >4 mg of protein for crystallization, which can be aided by using a 1.4 L Bioreactor (New Brunswick Scientific) to increase yield even further. To define optimal crystallization conditions and produce crystals suitable for X-ray diffraction analysis, a high-throughput crystallization lab (e.g., the lab at the Hauptman-Woodward Medical Research Institute (HWI), Buffalo, N.Y.) can be used. Such a state-of-the-art facility allows screening of as many as 400 crystallization droplets with less than a milligram of pure protein, which dramatically increases the chance to identify successful hits. Preliminary crystallization conditions found with the aid of the robot will be repeated in-house using hanging drop vapor diffusion technique and larger crystallization droplets (usually 4 ml versus the 0.5 ml drops set up by the robot). Crystals will be further optimized by varying the temperature of crystallization (between +4 and +22° C.) and screening crystallization additives. There are now a number of methods to successfully crystallize these proteins involving detergent solubilization of the relevant protein and subsequent use of ammonium sulfate or polyethylene glycol as crystallizing agent using the hanging drop procedure. The choice of detergent is important. Detergents producing crystals that diffract to higher resolution are non-ionic detergents such as octyl glucoside or lauryl dimethylamineoxide.[35] Use of high concentrations of small amphiphilic molecules has also been shown to positively influence the crystallization process. Use of non-detergent sulphobetaines (NDSB) or arginine for example has facilitated the formation of crystals suitable for X-ray crystallography.[36]

To solve the structure we will express and crystallize seleno-methionine derivatize protein and determine the structureby Single or Multiple Wavelength Anomalous Diffraction (SAD/MAD). If this fails, or if derivatization of the protein with seleno-methione is problematic (or if the seleno-methionine protein fails to crystallize), native crystals will be soaked into solutions containing 0.1-5 mM heavy atoms. A priority will be to use methyl mercury acetate, which is very soluble and selectively labels cysteine residues (there are two in Cit$_{Sc}$). In parallel, platinum tetraoxide, which is also very soluble and binds primarily to methionine, will be used. Derivatized crystals will be used to solve the structure by the classical Multiple Isomorphous Method (MIR). If both SAD/MAD and MIR methods fail, another approach will be to try to phase the structure with xenon gas using a combination of SAD/MAD and MIR methods.

The diffraction quality of the crystals will be characterized using an Excalibur PX Ultra X-ray tube. Medium resolution data to ~5 Å will be used for initial characterization of the crystal unit cell dimension, space group, and cell volume. Cryo-protection conditions that will allow collecting high quality data from single frozen crystals will also be defined. Higher resolution data will be measured using X-ray synchrotron radiation. Competitive beam-time is running at three national synchrotron radiation facilities, namely CHESS (Cornell High Energy Synchrotron Source), Stanford Synchrotron Radiation Laboratory, and the National Synchrotron Light Source. The aim of these experiments is to provide mechanistic insight into the differential recognition of citrate and metal-citrate. Understanding how this occurs and what conformational changes happen upon substrate binding would greatly forward the understanding of these unusual proteins.

Example 17

Investigations on Transcriptional Control of Cit$_{Sc}$

Transcriptional control may be through down regulation in the presence of glucose or up-regulation in the presence of both iron and citrate. The available sequence data for CitMHS bacteria explored to date was searched and a hypothesis is that transcription for CitMHS family members overall is regulated through at least three different mechanisms, not all of which are present in any given organism. CitM and CitH of B. subtilis, for example, appear to be regulated by catabolite control protein (CcpA), which binds to DNA and inhibits or promotes transcription, and a two-component response regulator CitST. Citrate induces the CitST regulator, which causes CitM expression but not in the presence of glucose. Cit$_{Sm}$ and Cit$_{Ef}$ appear to be regulated by the dual response and expression protein, CitO, which binds to an adenine rich area upstream of the genes and inhibits or expresses Cit$_{Sm}$ and Cit$_{Ef}$. An intriguing point here is that both Cit$_{Sm}$ and Cit$_{Ef}$ are known CcpA containing organisms but no recognizable catabolite responsive elements (cre sites) upstream of the genes have been found. Cit$_{Sc}$ expression is more ambiguous. Carbon catabolite repression (CCR) is not as well understood in *Streptomyces coelicolor* as it is in the case of *Bacillus subtilis*. Glucose kinase glkA has been suggested to have a role in CCR, however two PTS energy-coupling enzymes, enzyme I and HPr, have been identified and suggested to be involved in CCR. GlkA, galP1, gylRp, and vdh-Pare inactivated by glucose. When the promoter regions are aligned with Cit$_{Sc}$, the −35 regions are very similar and the −10 regions are *E. coli* $\theta^{70}$-like, as noted below:

```
                                                     (SEQ ID NO: 5)
    Cit_Sc -35 GGTGGGATGTTCAAGGGCGAACGTTAGGT -7

(SEQ ID NO: 6)
    galP1 GGGGGGTGGTGGGTTGTGATGTGTTATGT (SEQ ID NO: 7)
    gylRp GGCGGGAGGTCGGCATGGACCGGTAGTGT (SEQ ID NO: 8)
    vdh-P GGCGGGCCGGTACACCCAGGCTCTAATCT
```

Transport assays performed by Lensbouer et al. showed that *S. coelicolor* did not uptake divalent metal-citrate complexed in Strep Minimal Medium (SMM) with glucose as the only carbon source, but metal-citrate uptake was observed with *S. coelicolor* grown in SMM with citrate as the only carbon source.[54] However, uptake was observed with $Fe^{3+}$-citrate in both instances. An explanation for this would be that Cit$_{Sc}$ is being used to sequester iron. *S. coelicolor* uses DmdR1 and DmdR2 (Divalent metal dependent regulator protein) to regulate expression of iron related genes. The consensus sequence (Con) for DmdR1 and DmdR2, which is based on the comparison of the desA iron box from *Streptomyces pilos* and a genomic blast of *Streptomyces coelicolor*, is listed below with a putative promoter found upstream of $Cit_{Sc}$ as well as the diphtheriae toxin (Tox) and desA iron boxes for comparison. The fully conserved nucleotides are marked in bold/underline:

```
Cit_Sc  GCTGCTTCGCGCCACCTAA   (SEQ ID NO: 9)

Con     TTAGGTTAGGCTCACCTAA   (SEQ ID NO: 10)

desA    TTAGGTTAGGCTCACCTAA   (SEQ ID NO: 11)

Tox     TTAGGATAGCTTTACCTAA   (SEQ ID NO: 12)
```

Example 18

Flux Assays of K452C and R460C Mutated $Cit_{Sc}$ in E. coli

The R460C and K452C mutants were built using site-directed mutagenesis in a pUC19-$Cit_{Sc}$ vector. Upon isolation of the desired mutant, the gene was digested from pUC19 and ligated into pET-27b(+) to produce, upon overexpression, $Cit_{Sc}$ tagged with the pelB leader sequence. [14C]-citrate flux assays, as described earlier for *E. coli* (JW4251-2) expressing the native $Cit_{Sc}$, were then conducted following calcium uptake (Mg 'controls' and 'free' citrate controls were as for unmutated $Cit_{Sc}$). Results are shown in FIG. 8. What can be seen is the significant decrease in transported complex upon replacing the positively charged residues (R or K) with neutral C, consistent with the role of arginine and lysine in binding/recognition of the anionic, metal-citrate, substrate.

Example 19

Overexpression of $Cit_{Sc}$ in *E. coli* as a His-Tagged Protein

The open-reading frame (SCO1710) predicted as the metal-citrate transporter from *S. coelicolor* A3(2) was obtained from a third party supplier in cosmid vector StI30A. While there has been a huge advancement in methods designed to express and refold membrane proteins in recent years, traditionally there has been great difficulty both in obtaining significant yields of protein and also in obtaining the protein in the correctly folded state.

Expression in a number of vectors was attempted with expression proving successful using a slightly modified pET vector that produces a pelB leader sequence and His-tag at the target protein N-terminus and a pelB leader sequence at the N-terminus. This was built by combining elements of the pET15b+ and pET25b+ vectors. Optimization of expression conditions was conducted on a small scale (50 mL LB broth volumes) with IPTG concentration, temperature, length of induction and growth phase all trialed to maximize yield. Inductions at an $OD_{600}$ of 1.0 for 1 hour at 30° C. produced the most significant yields.

This affinity system has been shown to bind and release as required in the presence of various detergents, making it ideal for membrane protein purification. Since solubilizing the protein in functional form is the aim here, a number of detergents were trialed and their ability to produce fusion protein capable of binding to a nickel based IMAC column were tested. Detergents at a variety of critical micelle concentrations (CMC) were used, including β-octyl glucoside (OG), lauryl sarcosyl, CHAPS and Triton X-100. Ultimately, it was 10×CMC OG that proved the most successful. While higher temperatures (37° C.) were used in expression, solubilization was conducted at 4° C. because membrane proteins, especially those with several transmembrane domains, do not tolerate temperatures above this with irreversible denaturation often occurring.[43] Cells were harvested and lysed by sonication. Cell debris and soluble proteins were removed by centrifugation at 2000 g for 10 minutes at 4° C. and the membranes isolated at 50,000 g for 45 minutes at 4° C. Expression up to the Liter level has proven successful. Upon purification and cleavage of the tag, incorporation into right-side out (RSO) vesicles will be performed using the methods of Kabach.[44] The formation of so-called apoplastic side-out vesicles also allows the preparation of reasonably pure refolded membrane systems (~95%) by partitioning in aqueous polymer two-phase system. This was first demonstrated by Steck et al.[45] Should the RSO vesicles not prove successful, these ASO vesicles will be constructed.

Example 20

Discussion

Metal-Citrate Complex Transport by *Streptomyces coelicolor* A3(2)

With an ever-expanding family of metal-citrate transporters proteins being postulated by sequence homology studies[1], and with few examples of the family having been characterized to date, there is an opportunity to make a significant contribution to the fundamental understanding of inorganic complex uptake in biological systems.

It is believed that this is only the second example of a Gram-positive citrate transporter that preferentially uses ferric ions as a vital cofacter for transport. It is the first such member of the CitMHS to be successfully functionally characterized outside the native organism. It is also believed to be the first to show preferential metabolism of the transported $Fe^{3+}$-citrate species (over $Pb^{2+}$-citrate for example) when expressed heterologously. The $Fe^{3+}$-citrate species was also the only species transported above free citrate background when *S. coelicolor* was grown in SMM containing glucose and iron. The absence of iron from the broth in the same experiment greatly reduced subsequent $Fe^{3+}$-citrate uptake. This suggests *S. coelicolor* is using this system to acquire iron. While $Fe^{3+}$ was the dominant vital cofactor for transport, other metal ions with ionic radii of ~80 pm and greater ($Mn^{2+}$, $Ca^{2+}$, $Pb^{2+}$ and $Ba^{2+}$) were also transported. Assuming a high-spin, octahedral complex forms for $Fe^{3+}$-citrate this means an ionic radius of ~79 pm for iron. With the metal ions $Mg^{2+}$, $Ni^{2+}$ and $Co^{2+}$ not transported and having radii less than 72 pm, it appears then that there is an ionic radii role in determining transporter specificity.

Specificity does not correlate with the formation of bi- or tri-dentate complex formation since both the tridendate $Pb^{2+}$ and bidendate $Ca^{2+}$ and $Fe^{3+}$ are transported. This is in agreement with the work of Lolkema[46] and Francis.[40] Lolkema has instead described a "size criterion" that is the result of the physical size of the protein binding site as playing a major role in determining specificity.[4c] The difference in $Mn^{2+}$ and $Fe^{3+}$ transport, however, despite the similar ionic radii between the two metal ions, suggests that complex speciation and/or coordination geometry must play a part. The two most common citrate-to-metal binding motifs are a linear citrate backbone or one with the citrate backbone 'bent'. The manganese complex is found with the linear arrangement.[47] Iron-citrate structures described by Salifoglou et al. describe the citrate in the 'bent' arrangement for $Fe^{3+}$.[48] This may also explain the difference between $Fe^{3+}$ uptake over $Mn^{2+}$. Another potential effect may arise from complex charge with the manganese complex monovalent and the [Fe(III)(OH)$_2$-cit] complex both a mono- and a di-valent species. The presence of both a monovalent (68.2%) and divalent (31.8%) Fe-citrate species was calculated using MINTEQA2.[38] Interaction with the additional negative charge of the [Fe(III)(OH)$_2$-cit]$^{2-}$ complex may play some role in greater iron transport over manganese and indeed over other metals forming monovalent complexes (Ca$^{2+}$, Pb$^{2+}$, Ba$^{2+}$, Mg$^{2+}$, Co$^{2+}$, Ni$^{2+}$). Interestingly, it is the divalent species metabolized in studies in *P. fluorescens* conducted by Francis.[49]

*S. coelicolor* transports Fe$^{3+}$-citrate when grown in SMMG broth containing Fe$^{3+}$, but does not transport Fe$^{3+}$-citrate when Fe$^{3+}$ is omitted from the growth media. This suggests that the Cit$_{Sc}$ protein system may be used primarily to access iron and not to access citrate. The transformative nature of this determination lies in the importance of iron limitation in blocking infection by pathogenic bacteria. For example, a single injection of iron was shown to decrease the lethal dose of *Pseudomonas aeruginosa* (in a murine infection model) from more than 10$^4$ organisms to fewer than 10.[50] While not a pathogenic bacteria, *S. coelicolor* is a member of the Actinomycete family, which is related to bacteria such as *Neisseria meningitis*. The ability to access iron from iron citrate found in blood plasma would give *N. meningitis* a possible route to overcome iron-based bacteriostasis.[51] Chemical speciation models actually indicate that, amongst the naturally occurring low molecular mass ligands, a dominant Fe$^{3+}$-citrate species is formed at concentrations as low as 1 mM in serum.[52] An amino acid sequence homology study of the Cit$_{Sc}$ sequence against the *N. meningitis* and *B. anthracis* genome found sequences with up 56% amino acid homology. The open-reading frames from these bacteria were obtained (from IDT DNA) to express and functionally characterize them in *E. coli*. If they have members of the CitMHS family, these will be compared to the Fe$^{3+}$-citrate transporters of Cit$_{Sc}$ and Cit$_{Sm}$.

REFERENCES CITED

Citation of a reference herein shall not be construed as an admission that such reference is prior art to the present invention. All references cited herein are hereby incorporated by reference in their entirety. Below is a listing of references cited herein with reference number indicators:

A1. Altschul et al. 1997. *Nucleic Acids Res.* 25:3389-3402.
A2. Bandell et al. 1997. *J. Biol. Chem.* 272:18140-18146.
A3. Banin et al. 2005. *Proc. Natl. Acad. Sci. U.S.A.* 102: 11076-11081.
A4. Blancato et al. 2006. *FEBS Lett.* 273:5121-5130.
A5. Brown et al. 1984. *FEMS Microbiol. Lett.* 21:113-117.
A6. Ferguson et al. 2002. *Science.* 295:1715-1719.
A7. Forsberg et al. 1972. *J. Clin. Pathol.* 25:65-68.
A8. Francis et al. 1993. *Appl. Environ. Microbiol.* 59:109-113.
A9. Francis et al. 1992. *Nature.* 356:140-142.
A10. Glusker, J. P. 1980. *Acc. Chem. Res.* 13:345-352.
A11. Gruber et al. 2003. *Annu. Rev. Microbiol.* 57:441-466.
A12. Gustafsson, J. P. 2006. Visual MINTEQ 2.51, KTH, Dept. of Land and Water Resources Engineering. Stockholm, Sweden.
A13. Hao et al. 2000. *Transition Metal Chemistry* 26:384-387.
A14. Hopwood et al. 2002. *Nature.* 417:141-147.
A15. Joshi-Tope et al. 1995. *J. Bac.* 177:1989-1993.
A16. Kaneko et al. 2007. *J. Clin. Invest.* 117:877-888.
A17. Keiser et al. 2000. Chapter 19 p. 406. In Practical *Streptomyces* Genetics. Crowes Press, Norwich, U.K.
A18. Konigsberger et al. 2000. *J. Inorg. Biochem.* 78:175-184
A19. Krom et al. 2000. *J. Bacteriol.* 182:6374-6381.
A20. Korithoski et al. 2005. *J. Bacteriol.* 187:4451-4456.
A21. Krom et al. 2003. *Biochemistry.* 42:467-474.
A22. Li et al. 2002. *J. Membrane Biol.* 185: 9-16.
A23. Matzapetakis et al. 2000. *Inorg. Chem.* 39:4044-4051.
A24. Matzapetakis et al. 1998. *Am. Chem. Soc.* 120:13266-13267.
A25. Saier, M. H. Transport Classification Database. UC, San Diego: HTTP://tcdb.ucsd.edu.
A26. Singh et al. 2002. *Nature* 417:552-555.
A28. Xu et al. 2003. *Proc. Natl. Acad. Sci. U.S.A.* 100: 1286-1291.
A29. Fieschi et al. 1995. *J. Biol. Chem.* 270:30392-30400.
A30. Nivie're et al. 1999. *J. Biol. Chem.* 274:18252-18260.
A31. Warner et al. 2002. *Microbiology*, 148, 3405-3412.
1. Sequence and hydropathy analyses were performed on the Transport Classification Database website of Professor Milton H. Saier at UC, San Diego: tcdb.ucsd.edu.
2. Hopwood et al. *Nature* 2002, 417, 141-147.
3. (a) Marty-Teysset et al. *J. Biol. Chem.* 1995, 270, 25370-25376. (b) Bandell et al. *J. Biol. Chem.* 1997, 272, 18140-18146. (c) Bandell et al. *Biochemistry* 1999, 38, 10352-10360. (d) Bandell et al. *Biochemistry* 2000, 39, 13059-13067.
4. (a) Lolkema et al. *J. Bacteriol.* 2000, 182, 6374. (b) Korithoski et al. *Journal of Bacteriology* 2005, 187, 4451-4456. (c) Blancato et al. *FEBS Journal* 2006, 273, 5126.
5. (a) Magni et al. *FEMS Microbiol. Lett.* 1996, 142, 265. (b) van der Rest et al. *J. Biol. Chem.* 1992, 267, 8971.
6. Bandell et al. *J. Biol. Chem.* 2000, 275, 39130.
7. Bandell et al. *Biochemistry* 2000, 39, 13059.
8. Thompson et al. *Nucleic Acids Res.* 1994, 22, 4673.
9. Krom et al. *Biochemistry* 2003, 42, 467.
10. Grunewald et al. *Neuron* 1998, 21, 623.
11. Slotboom et al. *Proc. Natl. Acad. Sci.* (USA) 1999, 96, 14282.
12. Glusker, J. P. *Acc. Chem. Res.* 1980, 13, 345.
13. Francis et al. *Environ. Sci. Tech.* 1996, 30, 562.
14. Campi et al. *J. Inorg. Nucl. Chem.* 1964, 26, 553.
15. O'Brian et al. *J. Am. Chem. Soc.* 1997, 119, 12695.
16. Zhao-Hui et al. *Dalton Trans.* 2003, 2636.
17. Matzapetakis et al. *Inorg. Chem.* 1999, 38, 618.
18. Matzapetakis et al. *J. Am. Chem. Soc.* 1998, 120, 13266-13267.
19. Nunes et al. *Inorg. Chim. Acta.* 1987, 129, 283.
20. (a) Doyle et al. *Dalton Trans.* 2003, 22, 4230-4237. (b) Doyle et al. *Dalton Trans.* 2005, 3745-3750. (c) Doyle et al. *Inorg. Chem.,* 2001, 40, 1726-1727.
21. Tinoco et al. *Proc. Natl. Acad. Sci.* (USA) 2007, 105, 3268-3273.
22. Abramson et al. (2003) *Science* 301, 610-615.
23. Paadan et al. (2001) *Biochim. Biophys. Acta* 1505, 144-157.
24. Huang et al. (2003) *Science* 301, 616-620.
25. Yue et al. (2003) *J. Mol. Biol.* 332, 353-368.
26. Iwama et al. (2006) *J. Biol. Chem.* 281, 17727-17735.
27. Liu et al. (2005) *Biochemistry* 44, 2949-2962.
28. (a) Topology prediction was conducted on the EXPASY Proteomics server at us.expasy.org/using topology prediction software programs DAS, HMMTOP, TMAP, TMHMM, TMpred and TopPred. (b) Rost et al. *Nucleic acid Research* 2004, 32, 321.
29. Martell et al. Weinheim, N.Y. 1988.
30. Li et al. *J. Membrane Biol.* 2002, 185, 9.
31. Kaback et al. (1966) *Biochemistry* 55, 920-927.

32. Driessen et al. (1985) *Proc. Natl. Acad. Sci. USA* 82, 7555-7559.
33. Bandell et al. (1998) *Appl. Environ. Microbiol.* 64, 1594-1600.
34. Wang et al. *Biochemistry* 1999, 38, 10013.
35. Morgenen et al. *Biochemistry* 2005, 44, 4533.
36. Baalbaki et al. *J. Cryst. Growth* 1996, 168, 150-154.
37. Keiser et al. In *Practical Streptomyces Genetics* 2000 Chapter 19 p. 406, Crowes Press, Norwich, U.K.
38. Gustafsson, J. P. 2006. Visual MINTEQ 2.51, KTH, Dept. of Land and Water Resources Engineering. Stockholm, Sweden.
39. Li et al. *J. Membrane Biol.* 2002, 185, 9-16.
40. Francis et al. *Nature* 1992, 356, 140-142.
41. Ferguson et al. *Science* 2002, 295, 1715-1719.
42. Blancato et al. *FEBS Lett.* 2006, 273, 5121-5130.
43. Staudinger et al. *Methods in Molecular Biology* 2003, 228, 103-109.
44. Kaback, H. R. *Methods in Enzymology* 1971, 22, 99-120.
45. Steck et al. *Science* 1970, 168, 255-7.
46. Warner et al. *Microbiology* 2002, 148, 3405-3412.
47. Matzapetakis et al. *Inorg. Chem.* 2000, 39, 4044-4051.
48. Matzapetakis et al. *J. Am. Chem. Soc.* 1998, 120, 13266-13267.
49. Joshi-Tope et al. *J. Bacteriol.* 1995, 177, 1989-1993.
50. Forsberg et al. *J. Clin. Pathol.* 1972, 25, 65-68.
51. (a) Banin et al. *Proc. Natl. Acad. Sci.* (USA). 2005, 102, 11076-11081. (b) Brown et al. *FEMS Microbiol. Lett.* 1984, 21, 113-117. (c) Singh et al. *Nature* 2002, 417, 552-555.
52. Konigsberger et al. *J. Inorg. Biochem.* 2000, 78, 175-184.
53. Doyle et al. Isolation of DNA from *Bacillus subtilis* using the Wizard PLUS SV Miniprep DNA purification system *Promega eNOTES* July Edition 2007.
54. Doyle et al. *J. bacterial.* 2008, 190, 5616-5623.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An isolated antigen comprising:
a polypeptide consisting of a solvent exposed region from a metal-citrate transporter from *Streptomyces coelicolor*.

2. The isolated antigen according to claim 1, wherein said polypeptide consists of a solvent exposed region in the amino acid sequence of SEQ ID NO:1.

3. The isolated antigen according to claim 1, wherein said polypeptide consists of a solvent exposed region in the amino acid sequence encoded by SEQ ID NO:2.

4. The isolated antigen according to claim 1, wherein said polypeptide includes at least one amino acid residue selected from the group consisting of D75, D80, D111, N151, R161, Q438, H435, K452, H458, R460, and K464 of SEQ ID NO:1.

5. A pharmaceutical composition comprising: the antigen according to claim 1; and a pharmaceutically acceptable carrier.

* * * * *